United States Patent
Bhatia et al.

(10) Patent No.: US 11,510,687 B2
(45) Date of Patent: Nov. 29, 2022

(54) SURGICAL ROTARY CUTTING TOOL INCLUDING ARTICULABLE HEAD

(71) Applicant: Joint Preservation Innovations, LLC, Naperville, IL (US)

(72) Inventors: Sanjeev Bhatia, Naperville, IL (US); Peter J Millett, Edwards, CO (US)

(73) Assignee: JOINT PRESERVATION INNOVATIONS, LLC, Naperville, IL (US)

( * ) Notice: Subject to any disclaimer, the term of this patent is extended or adjusted under 35 U.S.C. 154(b) by 529 days.

(21) Appl. No.: 16/688,097

(22) Filed: Nov. 19, 2019

(65) Prior Publication Data

US 2022/0096099 A1 Mar. 31, 2022

Related U.S. Application Data

(60) Provisional application No. 62/768,609, filed on Nov. 16, 2018.

(51) Int. Cl.
*A61B 17/16* (2006.01)
*A61B 17/00* (2006.01)

(52) U.S. Cl.
CPC ...... *A61B 17/1631* (2013.01); *A61B 17/1615* (2013.01); *A61B 17/1664* (2013.01); *A61B 17/1675* (2013.01); *A61B 17/1682* (2013.01); *A61B 17/1684* (2013.01); *A61B 2017/00314* (2013.01); *A61B 2017/00327* (2013.01)

(58) Field of Classification Search
CPC .............. A61B 17/1615; A61B 17/162; A61B 17/1633
See application file for complete search history.

(56) References Cited

U.S. PATENT DOCUMENTS

| | | | |
|---|---|---|---|
| 5,916,146 A | 6/1999 | Allotta et al. | |
| 7,118,574 B2 | 10/2006 | Patel et al. | |
| 7,682,307 B2 | 3/2010 | Danitz et al. | |
| 7,785,252 B2 | 8/2010 | Danitz et al. | |
| 7,862,554 B2 | 1/2011 | Hegeman et al. | |
| 8,277,375 B2 | 10/2012 | Danitz et al. | |
| 2005/0165420 A1* | 7/2005 | Cha ............... | A61B 17/1633 606/150 |
| 2005/0261692 A1* | 11/2005 | Carrison ......... | A61B 17/1631 606/79 |
| 2007/0083081 A1 | 4/2007 | Schlagenhauf et al. | |

(Continued)

OTHER PUBLICATIONS

"TipControlTM Articulating Burr System" the non-patent, commercial reference you produced found at https://www.richardwolfusa.com.

*Primary Examiner* — Andrew Yang
(74) *Attorney, Agent, or Firm* — Morgan, Lewis & Bockius LLP

(57) ABSTRACT

An articulating rotary cutting tool configured to articulate a distal cutting tip upon a trigger being operated. The trigger can be locked into various articulating positions. The velocity of rotation of a cutting bit is substantially constant in both articulating and non-articulating positions. An articulation joint is one of a hex ball joint or a flexible spring joint. A button is included to release a locking pressure holding the trigger in a locked position. The trigger may employ articulating sliding surfaces that provide constraint to a flexed head in both directions of articulation.

39 Claims, 15 Drawing Sheets

(56) References Cited

U.S. PATENT DOCUMENTS

| | | | |
|---|---|---|---|
| 2009/0023988 A1* | 1/2009 | Korner | A61B 17/1633 600/114 |
| 2011/0022078 A1 | 1/2011 | Hinman | |
| 2016/0302876 A1 | 10/2016 | Teichtmann | |
| 2021/0128174 A1* | 5/2021 | Cannon | A61B 17/162 |

* cited by examiner

SURGICAL ROTARY CUTTING TOOL INCLUDING ARTICULABLE HEAD

CROSS-REFERENCE TO RELATED APPLICATION

This application claims the benefit of U.S. Provisional Patent Application Ser. No. 62/768,609, filed Nov. 16, 2018, which is incorporated herein in its entirety.

FIELD OF THE INVENTION

The present disclosure generally relates to surgical cutting tools, and more particularly to a surgical rotary cutting tool including an articulable head.

BACKGROUND OF THE INVENTION

Bone spurs typically develop in human joints and can frequently be a source of pain from impingement, disability and early degenerative wear of the joints. In situations where arthroscopic surgical intervention is required, these bone spurs are typically removed under direct arthroscopic visualization using straight arthroscopic burrs or angulated burrs in a fixed position. Unfortunately, the fixed nature of the burr limits the reach of the existing technology making it difficult or impossible to efficiently remove bone spurs in hard to reach areas. Additionally, when curved burrs are employed, they often do not fit in hard to reach areas due to the inability of the curve to be articulated straight on entry and exit.

In the shoulder, bone spurs typically develop on the undersurface of the acromion, the acromioclavicular joint and the inferior aspect of the humeral head. In the hip, bone spurs are usually most problematic at the rim of the acetabulum, the subspine area, and the femoral head-neck junction. In the ankle, bone spurs can occur in many areas but are frequently problematic at the anterior aspect of the tibiotalar joint. Other joints such as the knee and elbow, frequently also have problematic bone spurs that sometimes require arthroscopic resection.

Various types of mechanical joints exist that may be implemented in surgical cutting tools, or burrs, to articulate a cutting head of the tools. However, existing joints have low stability, wear quickly, produce too much vibration and noise, are limited in safe operation speeds, and are too complicated to manufacture. One common example of such joints is U-joints, which are known to have all of these problems. Further, U-joints cannot maintain a constant velocity of rotation at various angles.

More particularly, a universal joint cannot achieve a constant velocity of rotation at articulated angles because universal joints are inherently limited by mechanical inefficiency at high speeds, especially as they articulate beyond 15 degrees. Such properties predispose these universal joints to backlash and breakage in such situations. Due to limitations with wear and backlash, universal joints are not typically employed in settings of high RPM.

Therefore, there exists a need in the art for a surgical burr that solves the above described problems and eliminates the above described limitations, by providing a burr that has a cutting rotational velocity that remains constant at various different articulated positions.

SUMMARY OF THE INVENTION

This summary is provided to introduce a selection of concepts in a simplified form that are further described below in the detailed description. This summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

Disclosed is an articulating rotary cutting tool, comprising:
  an outer shaft having a proximal end and a distal end;
  at the distal end, a selectively articulable cutting head that is configured to articulate about a joint;
  at the proximal end, a controller;
  a cable extending between the articulable cutting head and the controller through the outer shaft;
  a drive shaft within the outer shaft extending between the proximal end and the distal end, the drive shaft attached to a rotary socket at the distal end for driving the rotary socket, the cable located between the drive shaft and the outer shaft, the drive shaft connectable to a driver at a proximal end of the drive shaft for being driven to translate rotational motion delivered by the driver to the articulable cutting head;
  wherein the cable is attached to the controller and the articulable cutting head such that operating the controller causes the cable to displace to selectively articulate the articulable cutting head about the joint; and
  wherein the articulable cutting head includes a rotary cutting bit and an articulable support that the rotary cutting bit rotates in relation to, the rotary cutting bit being configured to be rotationally driven by the rotary socket such that the rotary cutting bit is rotationally drivable by the rotary socket in both a non-articulated and an articulated position.

In another aspect, the rotary cutting bit and the articulable support articulate together upon the controller being operated.

In another aspect, the rotary socket is located inside the outer shaft at the distal end of the outer shaft.

In another aspect, the drive shaft and the rotary socket rotate about a longitudinal axis of rotation in relation to the outer shaft and the cable.

In another aspect, the drive shaft and rotary socket rotate in relation to the outer shaft and the cable to cause the rotary cutting bit to rotate in relation to the articulable support of the articulable cutting head in both an articulated and non-articulated position of the articulable cutting head.

In another aspect, the cable translates longitudinally in relation to the outer shaft to cause the articulable cutting head to articulate.

In another aspect, the articulating rotary cutting tool further comprises:
  a distal connector;
  wherein the distal connector is configured to connect the articulable cutting head to the distal end of the outer shaft; and
  wherein the distal connector includes a space to receive the cable therethrough for attaching a distal end of the cable to the articulable cutting head.

In another aspect, the joint has a joint axis of pivotation that passes through the rotary socket.

In another aspect, the rotary cutting bit pivotably attaches at a pivotal bit attachment point to a distal end of the rotary socket, such that the rotary cutting bit articulates by pivoting about the pivotal bit attachment point, about a bit axis of pivotation.

In another aspect, the articulable support is pivotably attached to the distal connector at opposing pivotal support attachment points, allowing the articulable support to pivotally articulate by pivoting about a support axis of pivotation that passes through the pivotal bit attachment point of the rotary cutting bit.

In another aspect, the articulable support and the rotary cutting bit share an axis of pivotation through a pivotal attachment point of the articulable support at the distal connector, and through the pivotal attachment point of the rotary cutting bit at the rotary socket.

In another aspect, the axis of pivotation passes through both pivotal attachment points of the articulable support and the rotary cutting bit.

In another aspect, the rotary cutting bit includes a rotary cutting bit groove, and the articulable support is configured to receive two parallel opposing bit pins on opposing sides of the articulable support, such that the rotary cutting bit is supported by the two bit pins contacting the rotary cutting bit groove while the rotary cutting bit is driven.

In another aspect, the rotary socket includes a groove, and the outer shaft is configured to receive two parallel opposing socket pins on opposing sides of the outer shaft, such that the rotary socket is supported by the socket pins contacting the rotary socket groove while the rotary socket is driven.

In another aspect, the rotary cutting bit is flexibly attached to the rotary socket by an intermediate flexible structure, the flexible structure acting as a flexible spring joint.

In another aspect, the flexible structure is a spring.

In another aspect, the controller includes a trigger that is pivotably attached to the outer shaft at opposing pivotal trigger attachment points such that the trigger pivots about a trigger pivotation axis.

In another aspect, a proximal end of the cable is attached to the trigger at a cable-trigger connection point, where the cable-trigger connection point is a point that is spaced away from the trigger pivotation axis, such that pulling the trigger causes the cable-trigger connection point to displace in relation to the trigger pivotation axis.

In another aspect, the controller includes a toothed slide connected to the trigger, and a proximal end plug that fixedly fits in the proximal end of the outer shaft, such that pulling the trigger displaces the toothed slide, wherein the proximal end plug has an external plug portion configured to snap into notches between teeth of the toothed slide such that pulling the trigger causes the external plug portion of the proximal end plug to snap into a next notch of the notches.

In another aspect, the proximal end plug is configured to receive the drive shaft freely therethrough.

In another aspect, a cable-trigger connecting slide is included in the controller to connect the cable to the trigger at the cable-trigger connection point, where the trigger is pivotably attached to the cable-trigger connecting slide, where the cable-trigger connecting slide is configured to receive the cable through a receiving space of the cable-trigger connecting slide, where the cable-trigger connecting slide also is connected to the toothed slide for displacing the toothed slide, and where pulling the trigger translates the cable-trigger connecting slide longitudinally in a direction away from the distal end of the outer shaft, to cause the toothed slide to translate.

In another aspect, the cable-trigger connecting slide is pivotably connected to the toothed slide to reduce lateral forces applied to the toothed slide by the cable-trigger connecting slide translating.

In another aspect, the articulating rotary cutting tool further comprises:

a second cable that is attached at one end to a spring at the proximal end of the outer shaft and attached at an opposite end of the second cable to an upper portion of the articulable cutting head laterally above the pivotal support attachment points and laterally above the pivotal bit attachment point, the second cable passing through the distal connector, the spring biasing the articulable cutting head toward a non-articulated position by applying a longitudinal biasing force having a force vector pointed away from the articulable cutting head, causing the trigger to be spring biased toward a non-articulating position, since a forward biasing force on the trigger is mechanically dependent on the spring biasing force applied by the spring through the second cable, through the articulable cutting head, and through the first cable.

In another aspect, the two cables are vertically aligned and parallel.

In another aspect, the spring bias applied by the second cable to the trigger by way of pulling the articulable cutting head causes the teeth of the toothed slide to be longitudinally force-biased against the external plug portion, such that pulling the trigger can overcome the spring bias and snap the external plug portion between the teeth, and such that the trigger is selectively lockable into a next notch between the teeth.

In another aspect, the controller further includes a spring biased button that arcs over the drive shaft and contacts the toothed slide such that when the button is pressed the toothed slide translates laterally away from the drive shaft such that the toothed slide releases from being longitudinally forced against the external plug portion causing the trigger to translate back to the non-articulating position due to the spring bias applied by the spring and the second cable, allowing a user to subsequently pull the trigger to selectively lock the toothed slide behind the external plug portion in increments set by a spacing of the teeth to one or more articulated positions set by the spacing of the teeth, and such that the user may press the spring biased button again to release the toothed slide from being longitudinally forced against the external plug portion and be displaced back into the non-articulating position by way of a spring force applied through the second cable by the spring.

In another aspect, the controller further includes:

a second spring biasing the toothed slide upwards, laterally, to allow the teeth to be laterally forced against the external plug portion and to allow the external plug portion to contact a top surface of the toothed slide, to allow the teeth to apply a longitudinal force against the external plug portion due to the spring bias of the first spring, such that the button contacts a top surface of the toothed slide to cause the toothed slide to displace downward against the second spring when the button is pressed to release the teeth from being longitudinally forced against external plug portion.

In another aspect, the second spring receives a perpendicular, laterally, and downwardly extending portion of the toothed slide such that the second spring applies a longitudinal resistive force to the downwardly extending portion of the toothed slide when the trigger is pulled.

In another aspect, the proximal end plug houses the first spring and a front portion of the cable-trigger connecting slide, and a proximal end of the first spring is attached to a proximal portion of the proximal end plug.

In another aspect, the articulating rotary cutting tool further comprises:

a second cable attached to a second cable-trigger connection point on the trigger, such that the second cable-trigger connection point is opposite to the first cable-trigger connection point of the first cable with respect to the trigger pivotation axis, where the second cable-trigger connection point is spaced away from the trigger pivotation axis, such that operating the trigger causes the first cable-trigger connection point and the second cable-trigger connection point to displace in opposite directions to selectively articulate the cutting head between non-articulated and articulated positions.

In another aspect, the controller includes a toothed arm, such that pushing a button displaces the toothed arm, wherein a proximal end of the trigger is configured to snap into notches between teeth of the toothed arm such that pulling or pushing the trigger causes the proximal end of the trigger to snap into a next notch, respectively, wherein operating the button releases pressure between the proximal end of the trigger and the toothed arm to allow the trigger to more freely move with respect to the toothed arm.

In another aspect, the toothed arm is curved, matching an arc travelable by the proximal end of the trigger.

In another aspect, the button is configured to receive the drive shaft freely therethrough, and includes two sets of horizontal lateral extensions, one set on each side, such that two opposing longitudinal extensions of the toothed arm are each respectively received in a gap between each set of horizontal extensions of the button, to allow the button to press down and up on the longitudinal extensions of the toothed arm.

In another aspect, the toothed arm arcs over, and is pivotably attached to a toothed arm attachment point at opposing outer surfaces of the outer shaft between the longitudinal extensions and a distal portion of the toothed arm, such that pressing down on the longitudinal extensions via the button and upper horizontal extensions of the button causes the distal portion to rise, and wherein the button is spring biased laterally upward via a spring to bias the longitudinal extensions upward via lower horizontal extensions of the button, for maintaining an appropriate pressure between the distal portion of the toothed arm and the proximal end of the trigger, the toothed arm attachment point being a fulcrum point for the toothed arm pivoting according to pressing or releasing the button.

In another aspect, the cables each have ball ends to prevent the cables from passing through their respective connection points.

In another aspect, a proximal end of the drive shaft is covered by a housing.

In another aspect, the controller includes a housing to secure its components, while exposing the button, the trigger, a proximal portion of the drive shaft, the housing of the drive shaft, forward portions of the outer shaft, and the articulable cutting head.

In another aspect, a sheath may be fixedly attached to the articulable support to block non-cutting portions of the articulable support.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION

Figure 1:
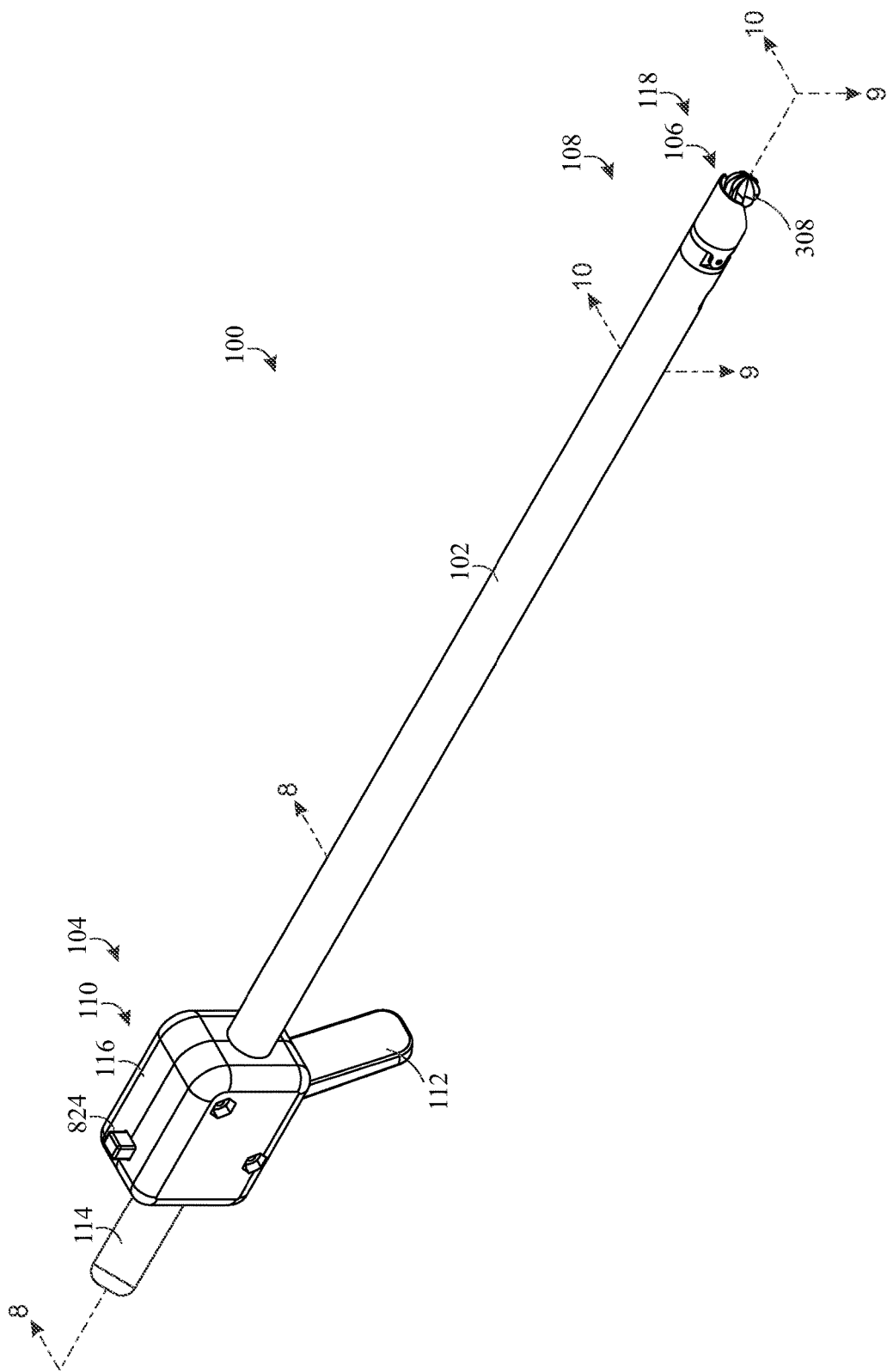
FIG. 1 presents a top perspective view of an articulating rotary cutting tool having a ball joint at an articulable cutting head and a spring-biased trigger, in accordance with aspects of the present disclosure.
Figure 2:
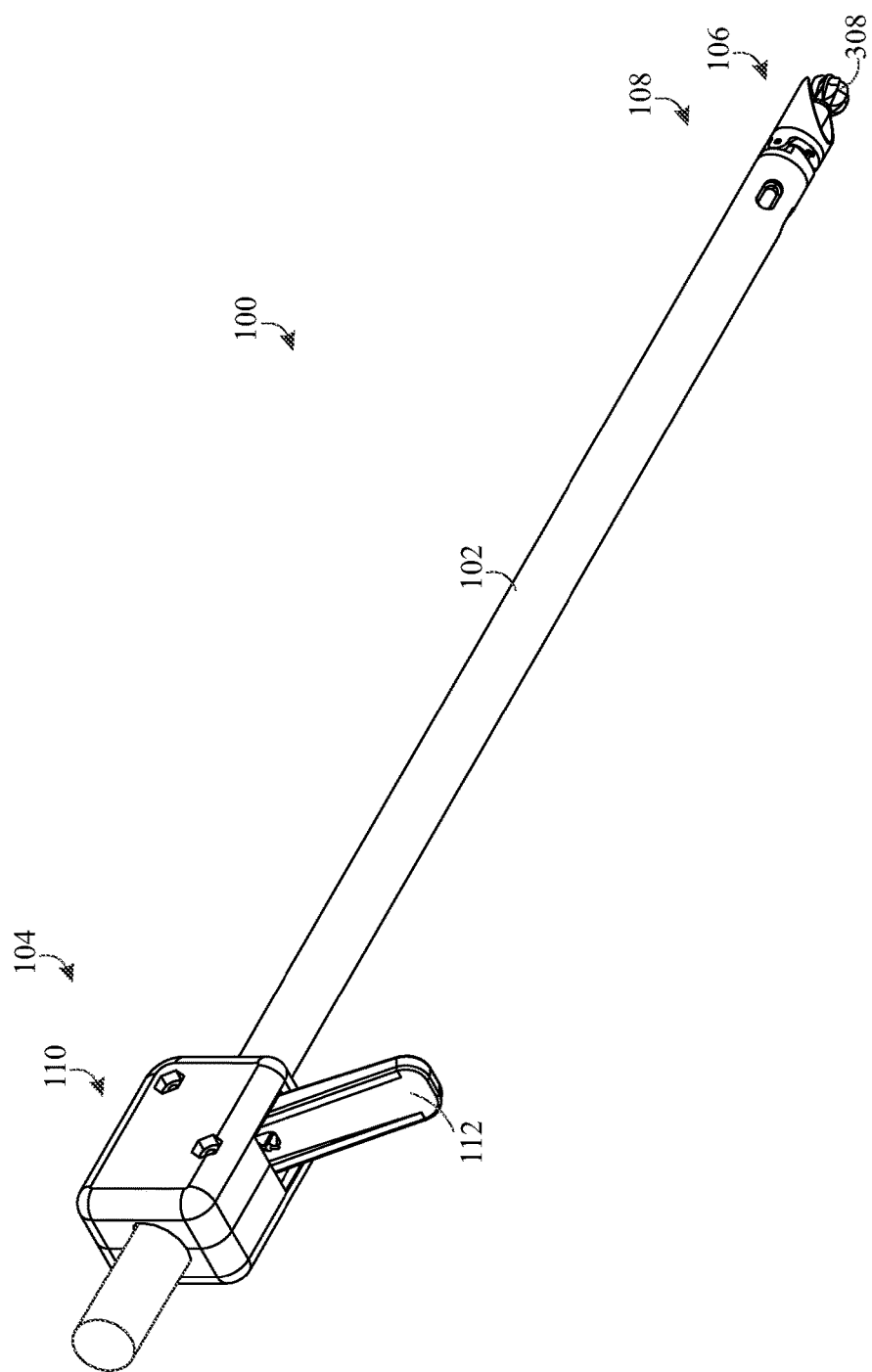
FIG. 2 presents a bottom perspective view of the articulating cutting tool of FIG. 1, in accordance with aspects of the present disclosure.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As shown throughout FIGS. 1-17, disclosed is an articulating rotary cutting tool 100. The rotary cutting tool 100 may include an outer shaft 102 having a proximal end 104 and a distal end 108, and at the distal end 108, a selectively articulable cutting head 106 that is configured to articulate about a joint 502 (FIG. 5). The rotary cutting tool 100 may include, at the proximal end 104, a controller 110, and a first cable 302 (FIG. 3) extending between the articulable cutting head 106 and the controller 110 through the outer shaft 102. It is to be understood that any of the herein described cables could be a longitudinal rigid or semi-rigid structure, such as a push-pull rod.

Figure 3:
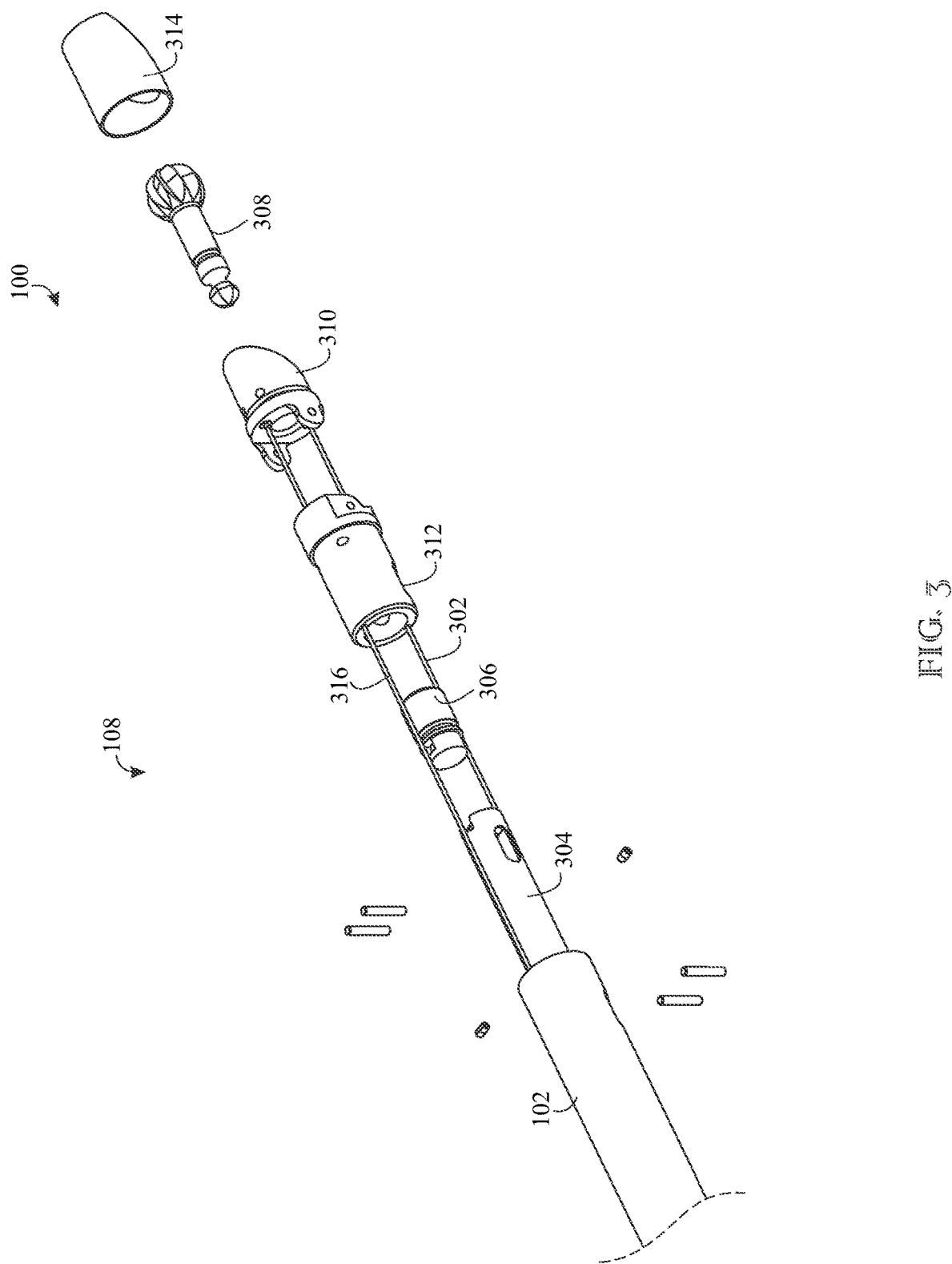
FIG. 3 presents an exploded view of various parts of distal portions of the articulating cutting tool of FIG. 1, in accordance with aspects of the present disclosure.
Figure 16:
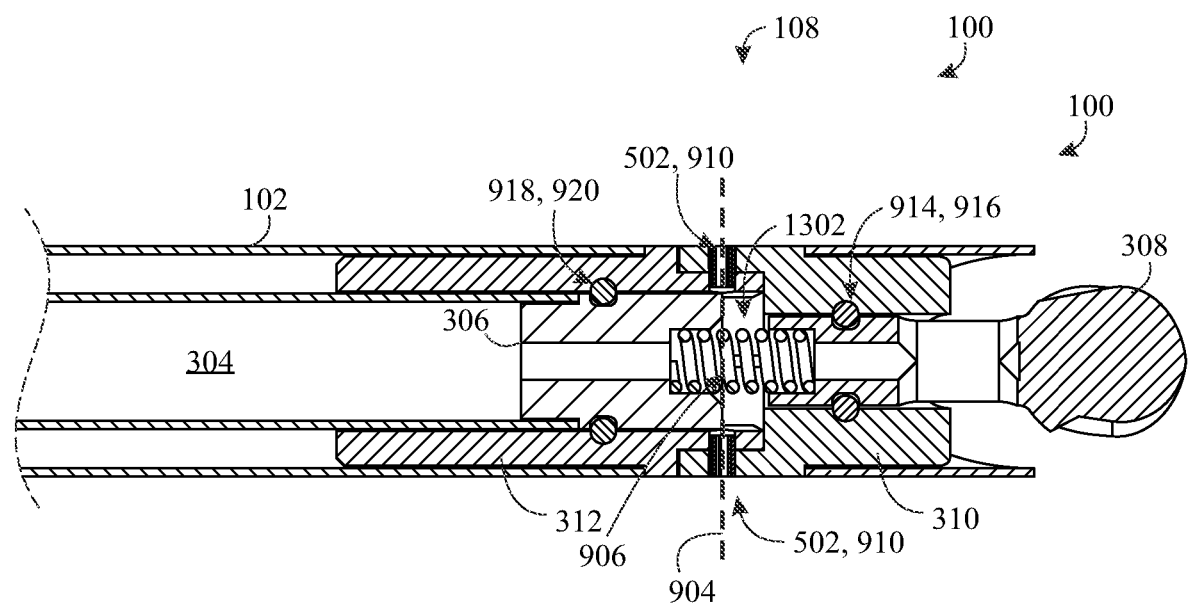
FIG. 16 presents a cross sectional view of a distal end of the articulating cutting tool of FIG. 11, where the cross section is taken along longitudinal cross sectional plane 16-16 of FIG. 11, in accordance with aspects of the present disclosure.
Figure 17:
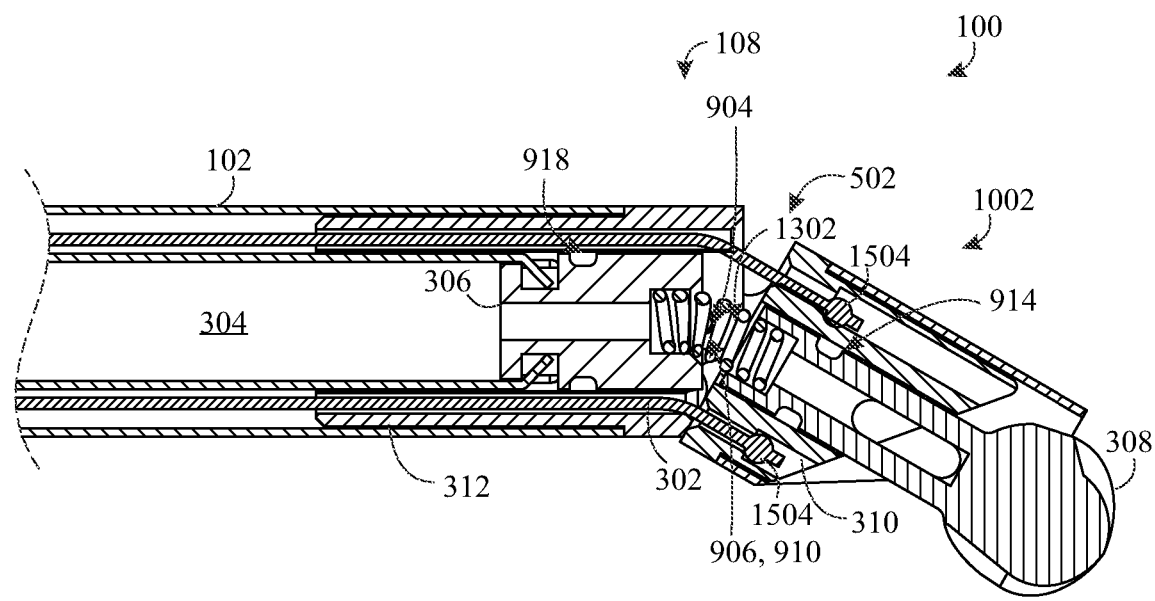
FIG. 17 presents a cross sectional view of a distal end of the articulating cutting tool of FIG. 11, where the articulable cutting head is in an articulated position, where the cross section is taken along longitudinal cross sectional plane 17-17 of FIG. 11, in accordance with aspects of the present disclosure.

The rotary cutting tool 100 may include a drive shaft 304 (FIGS. 3 and 4) within the outer shaft 102 extending between the proximal end 104 and the distal end 108. The drive shaft 304 may be attached to a rotary socket 306 (FIG. 3) at the distal end 108 for driving the rotary socket 306. As shown in FIGS. 16 and 17, the rotary socket 306 may have an internal hollow space to favorably change (e.g. increase) the rotational inertia of the rotary socket 306. The first cable 302 may be located between the drive shaft 304 and the outer shaft 102 (FIG. 3). A second cable 316 is also shown in FIG. 3, between the drive shaft 304 and the outer shaft 102. The drive shaft 304 may be connectable to a driver 802 at a proximal end of the drive shaft 304 for being driven to translate rotational motion delivered by the driver 802 to the articulable cutting head 106.

It is to be understood that the rotary socket 306 and the drive shaft 304 may be integrated in one piece. In other words, the drive shaft 304 may have a rotary socket configuration at its distal end to effect the functionalities described herein, without departing from the spirit or scope of this disclosure. For example such a rotary socket configuration integrated in the drive shaft 304 may have any structure, element, or configuration of the rotary socket 306 to effect the functionalities disclosed herein of the rotary socket 306 and connected parts.

The first cable 302 may be attached to the controller 110 (FIG. 8) and the articulable cutting head 106 such that operating the controller 110 causes the first cable 302 to displace to selectively articulate the articulable cutting head 106 about the joint 502 (FIG. 5). The first cable 302 may translate longitudinally in relation to the outer shaft 102 to cause the articulable cutting head 106 to articulate.

Figure 9:
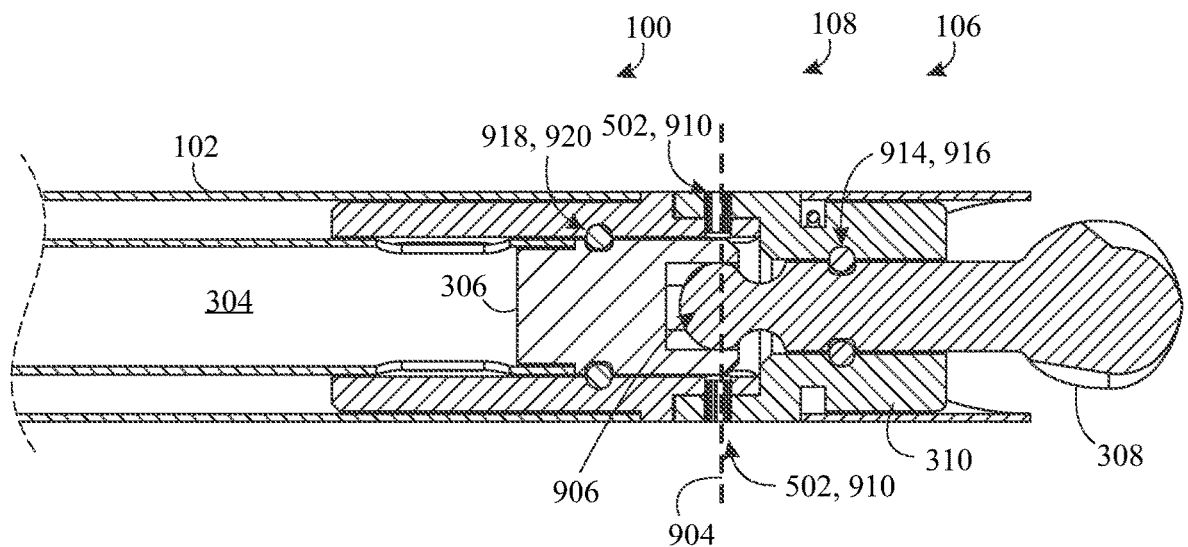
FIG. 9 presents a cross sectional view of a distal end of the articulating cutting tool of FIG. 1, where the cross section is taken along longitudinal cross sectional plane 9-9 of FIG. 1, in accordance with aspects of the present disclosure.
Figure 10:
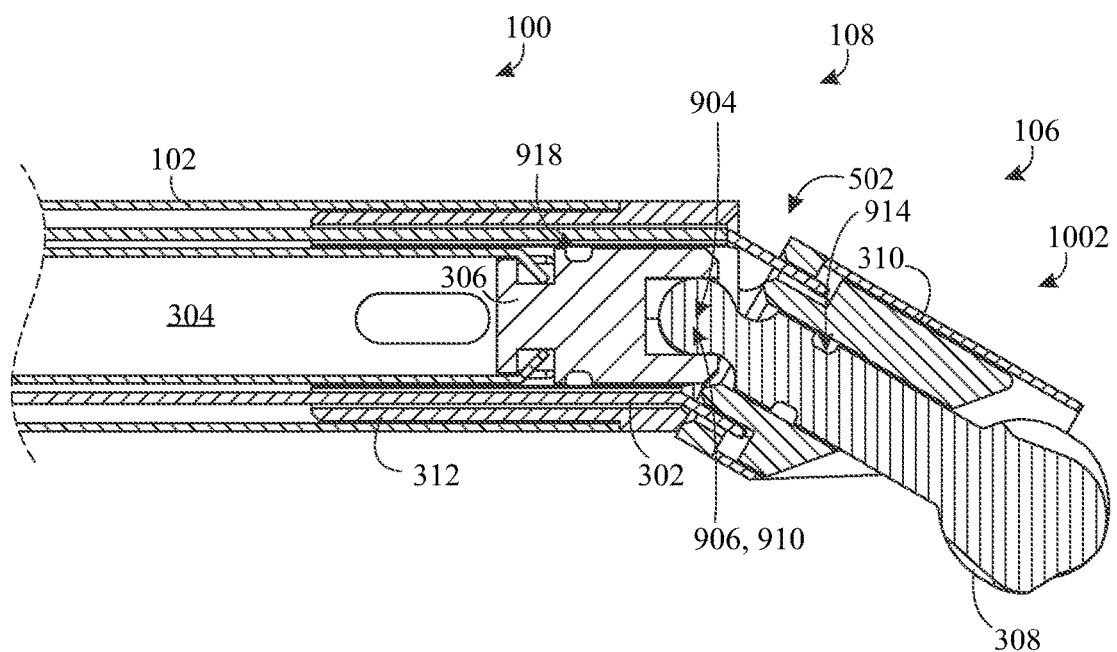
FIG. 10 presents a cross sectional view of a distal end of the articulating cutting tool of FIG. 1, where the articulable cutting head is in an articulated position, where the cross section is taken along longitudinal cross sectional plane 10-10 of FIG. 1, in accordance with aspects of the present disclosure.

The articulable cutting head 106 may include a rotary cutting bit 308 and an articulable support 310 that the rotary cutting bit 308 rotates in relation to (FIGS. 9 and 10). The rotary cutting bit 308 may be configured to be rotationally driven by the rotary socket 306 such that the rotary cutting bit 308 is rotationally drivable by the rotary socket 306 in both a non-articulated 118 (FIG. 1) and an articulated position 1002 (FIG. 10). The rotary cutting bit 308 and the articulable support 310 may articulate together upon the controller 110 being operated (FIG. 10). As shown in FIGS. 16 and 17, the rotary cutting bit 308 may have an internal hollow space to favorably change (e.g. increase) the rotational inertia of the rotary cutting bit 308.

The rotary socket 306 may be located inside the outer shaft 102 at the distal end 108 of the outer shaft 102 (FIGS. 9 and 10). The drive shaft 304 and the rotary socket 306 may rotate about a longitudinal axis of rotation in relation to the outer shaft 102 and the cables 302 and 316. The drive shaft 304 and rotary socket 306 may rotate in relation to the outer shaft 102 and the cables 302 and 316 to cause the rotary cutting bit 308 to rotate in relation to the articulable support 310 of the articulable cutting head 106 in both an articulated (FIG. 10) and non-articulated (FIG. 9) position of the articulable cutting head 106.

The articulating rotary cutting tool 100 may include a distal connector 312 (FIG. 3). The distal connector 312 may be configured to connect the articulable cutting head 106 to the distal end 108 of the outer shaft 102 (FIG. 9).

The distal connector 312 may include a space to receive the first cable 302 and the second cable 316 therethrough for attaching a distal end of the first cable 302 and the second cable 316 to the articulable cutting head 106 (FIG. 10).

The joint 502 may have a joint axis 904 that passes through the rotary socket (FIG. 9). The rotary cutting bit 308 may pivotably attach at a pivotal bit attachment point 906 to a distal end of the rotary socket 306, such that the rotary cutting bit 308 articulates by pivoting about the pivotal bit attachment point 906, about the joint axis (FIGS. 9 and 10).

The articulable support 310 may be pivotably attached to the distal connector 312 at opposing pivotal support attachment points 910, allowing the articulable support 310 to pivotally articulate by pivoting about the joint axis 904 that passes through the pivotal bit attachment point 906 of the rotary cutting bit 308 (FIGS. 9 and 10). The articulable support 310 and the rotary cutting bit 308 may share an axis of pivotation through a pivotal attachment point 910 of the articulable support 310 at the distal connector 312, and through the pivotal attachment point 906 of the rotary cutting bit 308 at the rotary socket 306 (FIGS. 9 and 10).

The rotary cutting bit 308 may include a rotary cutting bit groove 914 (FIGS. 9 and 10), and the articulable support 310 may be configured to receive two parallel opposing bit pins 916 on opposing sides of the articulable support 310, such that the rotary cutting bit 308 is supported by the two bit pins 916 contacting the rotary cutting bit groove 914 while the rotary cutting bit 308 is driven (FIGS. 9 and 10). The rotary socket 306 may include a rotary socket groove 918 (FIGS. 9 and 10), and the outer shaft 102 may be configured to receive two parallel opposing socket pins 920 on opposing sides of the outer shaft 102, such that the rotary socket 306 is supported by the socket pins 920 contacting the rotary socket groove 918 while the rotary socket 306 is driven (FIGS. 9 and 10).

Figure 13:
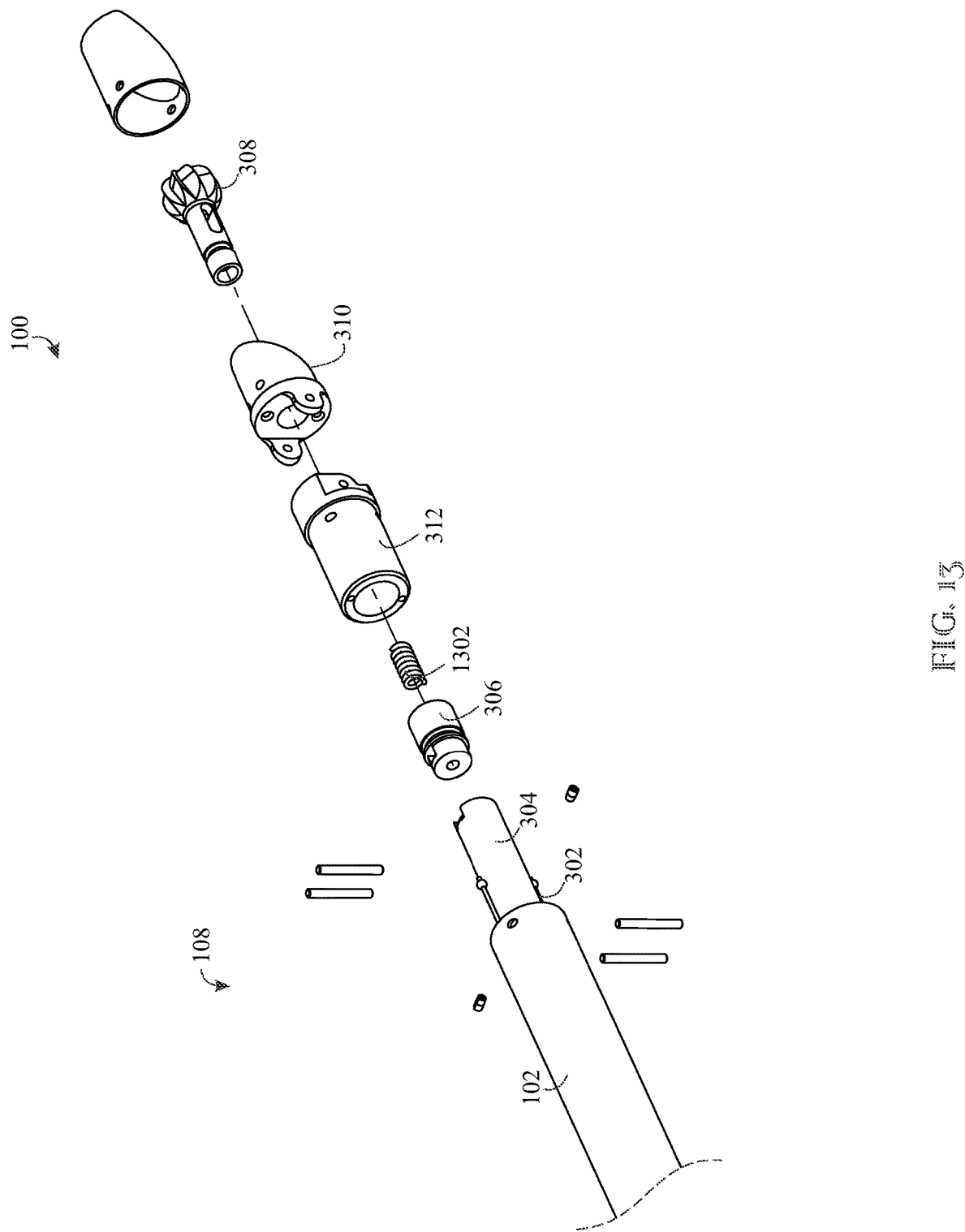
FIG. 13 presents an exploded view of various parts of distal portions of the articulating cutting tool of FIG. 11, in accordance with aspects of the present disclosure.

The rotary cutting bit 308 may be flexibly attached to the rotary socket 306 by an intermediate flexible structure 1302 (FIGS. 13, 16, and 17). The flexible structure 1302 may act as a flexible spring joint. The flexible structure may be a spring.

Figure 4:
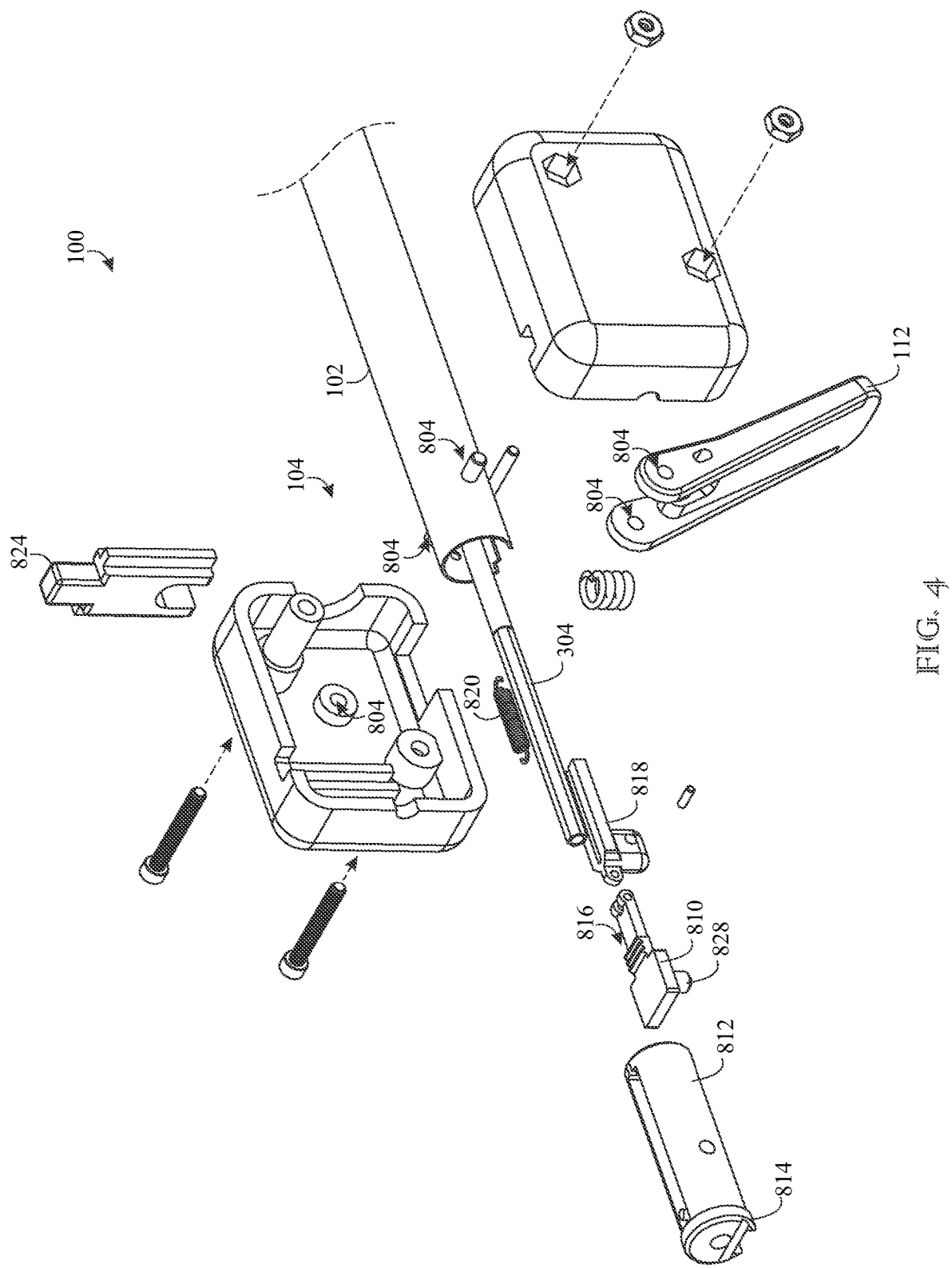
FIG. 4 presents an exploded view of various parts of proximal portions of the articulating cutting tool of FIG. 1, in accordance with aspects of the present disclosure.
Figure 5:
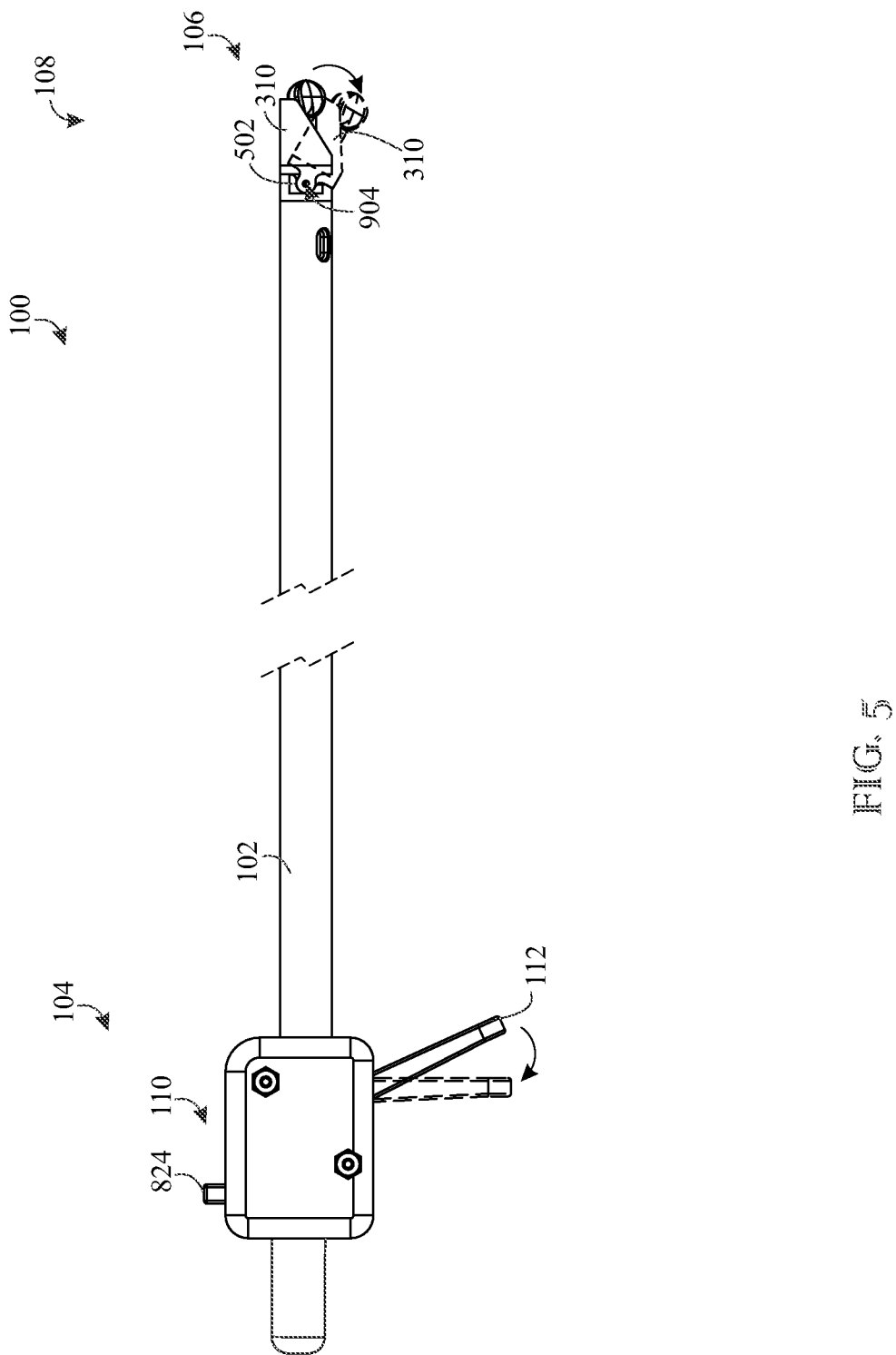
FIG. 5 presents a side elevation view of the articulating cutting tool of FIG. 1, where the trigger is being pulled to cause the articulable cutting head to articulate downward, in accordance with aspects of the present disclosure.
Figure 6:
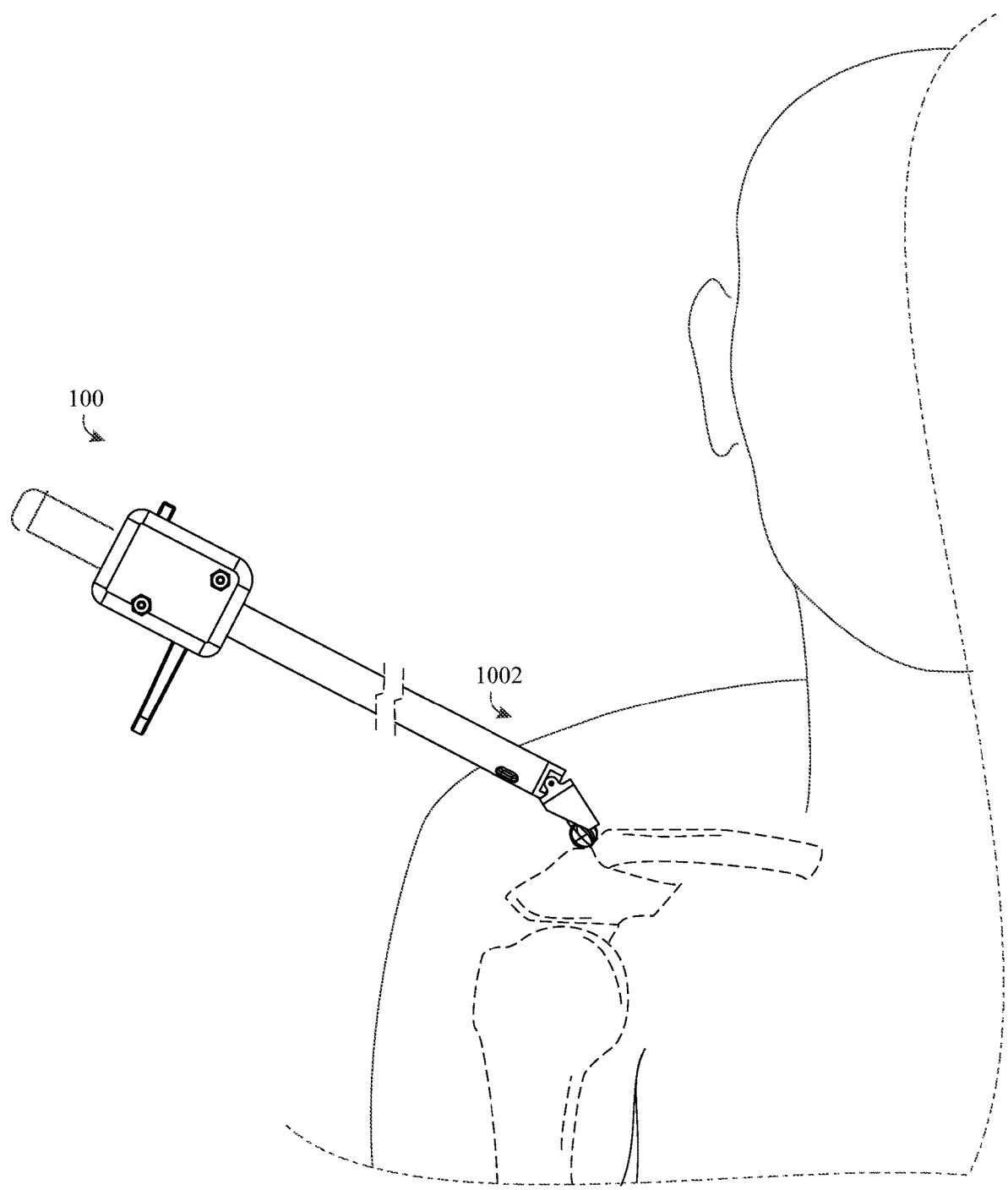
FIG. 6 presents exemplary use of an articulating cutting tool on a shoulder joint, in accordance with aspects of the present disclosure.
Figure 7:
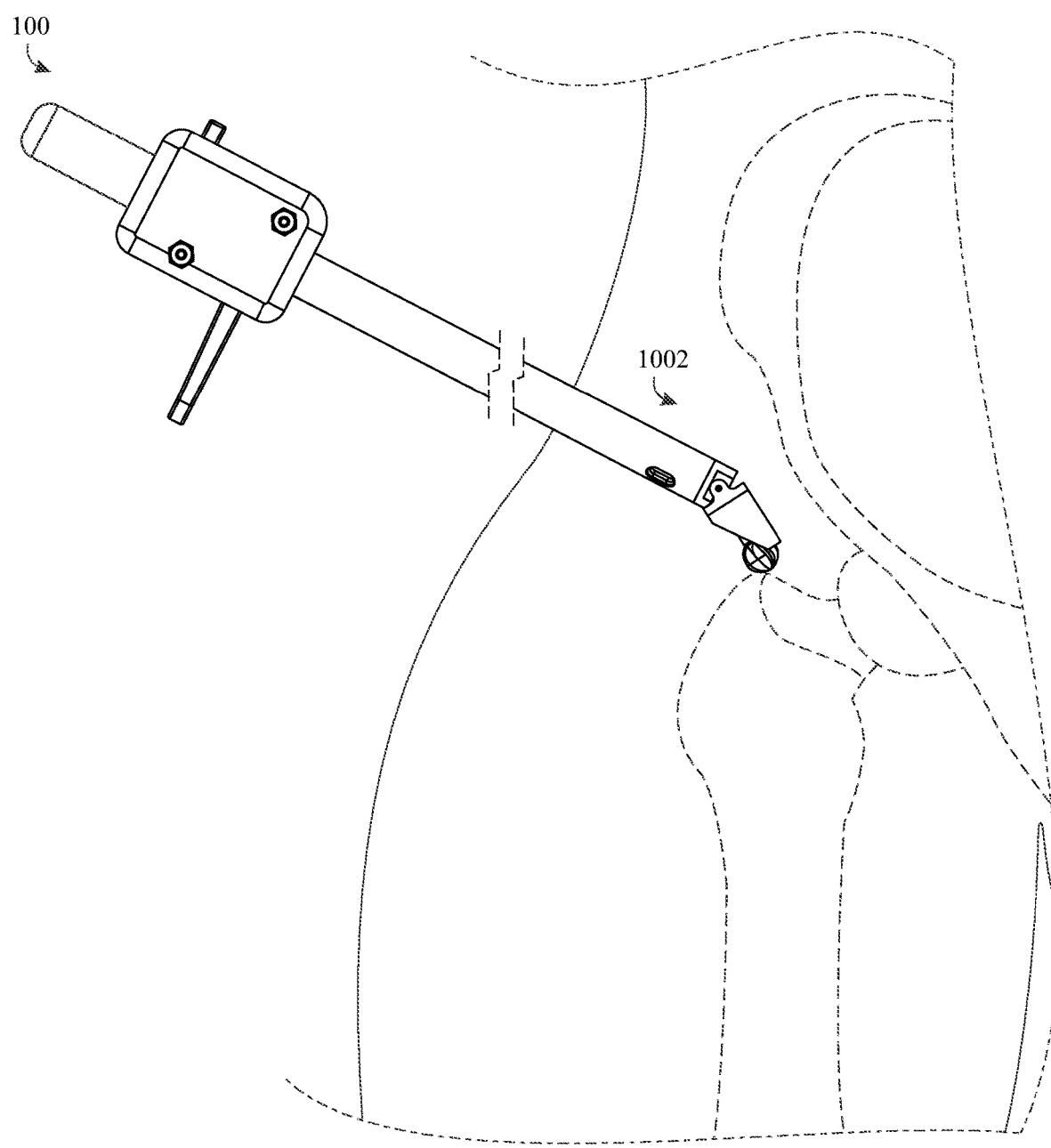
FIG. 7 presents exemplary use of an articulating cutting tool on a hip joint, in accordance with aspects of the present disclosure.
Figure 8:
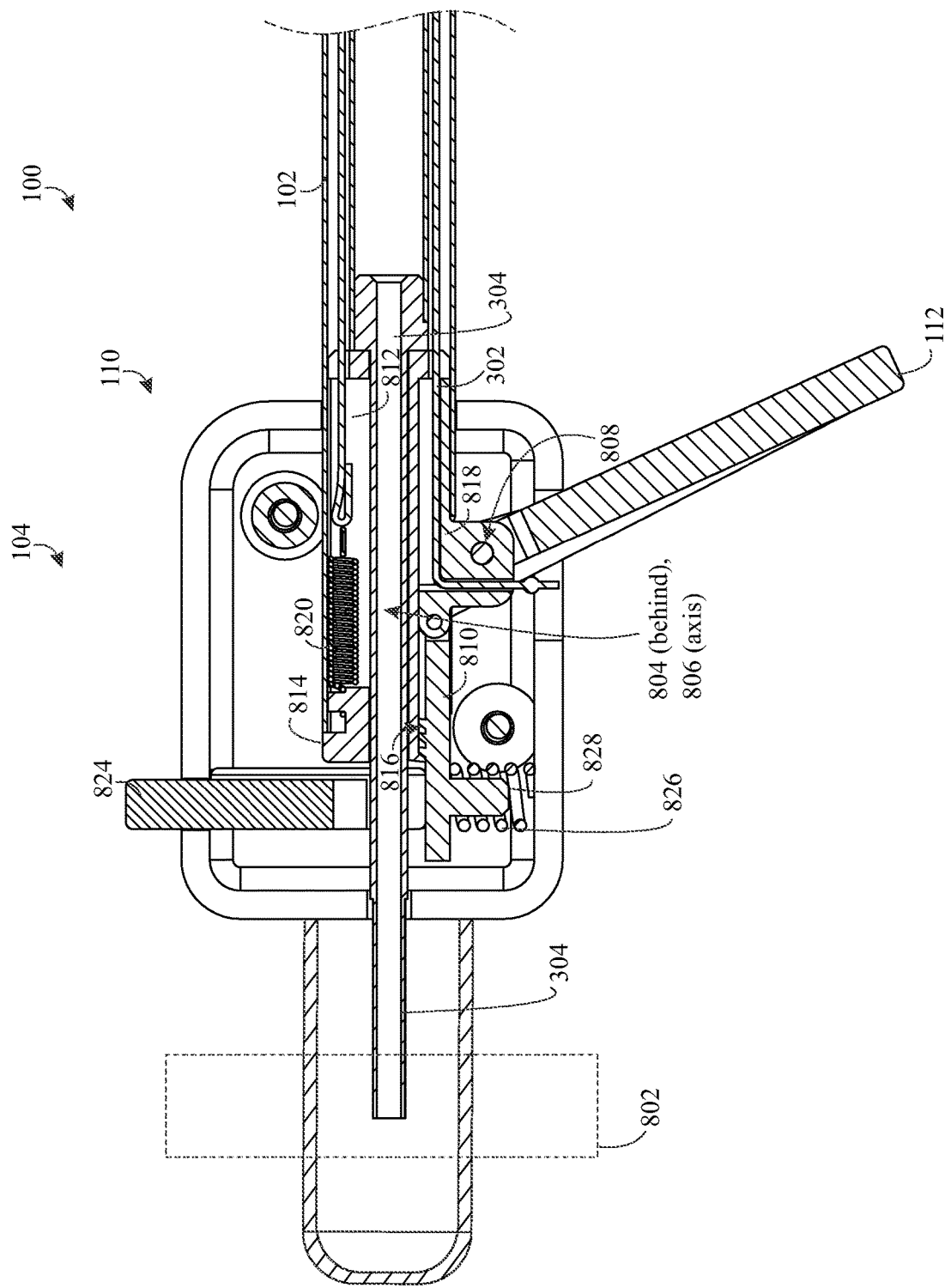
FIG. 8 presents a cross sectional view of a controller of the articulating cutting tool of FIG. 1, where the cross section is taken along longitudinal cross sectional plane 8-8 of FIG. 1, in accordance with aspects of the present disclosure.

The controller 110 may include a trigger 112 that is pivotably attached to the outer shaft 102 at opposing pivotal trigger attachment points 804 such that the trigger 112 pivots about a trigger pivotation axis 806 (FIGS. 4 and 8).

A proximal end of the first cable 302 may be attached to the trigger 112 at a cable-trigger connection point 808, where the first cable-trigger connection point 808 is a point that is spaced away from the trigger pivotation axis 806, such that pulling the trigger 112 causes the first cable-trigger connection point 808 to displace in relation to the trigger pivotation axis 806 (FIG. 8).

The controller 110 may include a toothed slide 810 connected to the trigger 112, and a proximal end plug 812 that fixedly fits in the proximal end 104 of the outer shaft 102, such that pulling the trigger 112 displaces the toothed slide 810 (FIG. 8). The proximal end plug 812 may have an external plug portion 814 configured to snap into notches between teeth 816 of the toothed slide 810 such that pulling the trigger 112 causes the external plug portion 814 of the proximal end plug 812 to snap into a next notch of the notches between the teeth 816. The proximal end plug 812 may be configured to receive the drive shaft 304 freely therethrough (FIGS. 4, and 8).

A first cable-trigger connecting slide 818 may be included in the controller 110 to connect the first cable 302 to the trigger at the first cable-trigger connection point 808 (FIG. 8). The trigger 112 may be pivotably attached to the first cable-trigger connecting slide 818. The first cable-trigger connecting slide 818 may be configured to receive the first cable 302 through a receiving space of the first cable-trigger connecting slide 818. The first cable-trigger connecting slide 818 also may be connected to the toothed slide 810 for displacing the toothed slide 810. Pulling the trigger 112 may translate the first cable-trigger connecting slide 818 longitudinally in a direction away from the distal end 108 of the outer shaft 102, to cause the toothed slide 810 to translate. The first cable-trigger connecting slide 818 may be pivotably connected to the toothed slide 810 to reduce lateral force applied to the toothed slide 810 by the first cable-trigger connecting slide 818 translating (FIG. 8).

The articulating rotary cutting tool 100 may further include a second cable 316 that is attached at one end to a first spring 820 at the proximal end 104 of the outer shaft 102 and attached at an opposite end of the second cable 316 to an upper portion of the articulable cutting head 106 laterally above the pivotal support attachment points 910 and laterally above the pivotal bit attachment point 906 (FIG. 8). The second cable 316 may pass through the distal connector 312. The first spring 820 may bias the articulable cutting head 106 toward a non-articulated position 118 by applying a longitudinal biasing force having a force vector pointed away from the articulable cutting head 106, causing the trigger 112 to be spring biased toward a non-articulating position 118. A forward biasing force on the trigger 112 is mechanically dependent on the spring biasing force applied by the first spring 820 through the second cable 316, through pivoting the articulable cutting head 106, and through the first cable 302. The two cables may be vertically aligned and parallel (FIG. 8).

The spring bias applied by the second cable 316 to the trigger 112 by way of pulling the articulable cutting head 106 may cause the teeth 816 of the toothed slide 810 to be longitudinally force-biased against the external plug portion 814, such that pulling the trigger 112 can overcome the spring bias and snap the external plug portion 814 between the teeth 816, and such that the trigger 112 is selectively lockable into a next notch between the teeth 816.

The controller 110 may further include a spring biased button 824 that arcs over the drive shaft 304 and contacts the toothed slide 810 such that when the button 824 is pressed the toothed slide 810 translates laterally away from the drive shaft 304, such that the toothed slide 810 releases from being longitudinally forced against the external plug portion 814 causing the trigger to translate back to the non-articulating position 118 due to the spring bias applied by the first spring 820 and the second cable 316 (FIG. 8). This allows a user to subsequently pull the trigger 112 to selectively lock the toothed slide 810 behind the external plug portion 814 in increments set by a spacing of the teeth 816 to one or more articulated positions set by the spacing of the teeth 816, such that the user may press the spring biased button 824 again to release the toothed slide 810 from being longitudinally forced against the external plug portion 814 and be displaced back into the non-articulating position 118 by way of a spring force applied through the second cable 316 by the first spring 820.

The controller may further include a second spring 826 biasing the toothed slide 810 upwards (FIG. 8), laterally, to allow the teeth 816 to be laterally forced against the external plug portion 814 and to allow the external plug portion 814 to contact a top surface of the toothed slide 810, to allow the teeth 816 to apply a longitudinal force against the external plug portion 814 due to the spring bias of the first spring 820, such that the button 824 contacts a top surface of the toothed slide 810 to cause the toothed slide 810 to displace downward against the second spring 826 when the button 824 is pressed to release the teeth 816 from being longitudinally forced against the external plug portion 814.

The second spring 826 may receive a perpendicular, laterally, and downwardly extending portion 828 of the toothed slide 810 such that the second spring 826 applies a longitudinal resistive force to the downwardly extending portion 828 of the toothed slide 810 when the trigger 112 is pulled (FIG. 8).

The proximal end plug 812 may house the first spring 820 and a front portion of the first cable-trigger connecting slide 818. A proximal end of the first spring 820 may be attached to a proximal portion of the proximal end plug 812.

Figure 11:
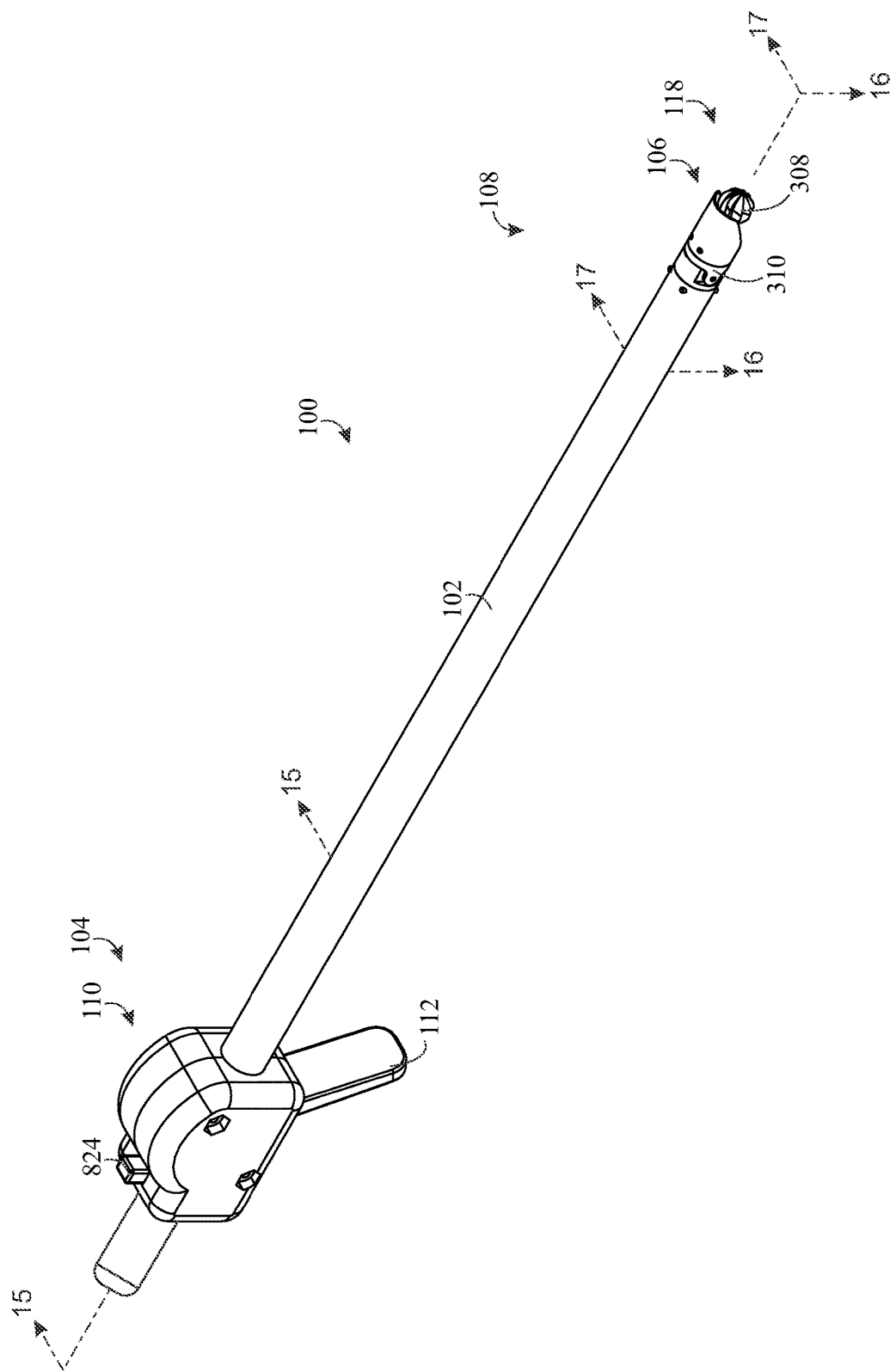
FIG. 11 presents a top perspective view of an articulating rotary cutting tool having a flexible joint at an articulable cutting head and a non-spring-biased trigger, in accordance with aspects of the present disclosure.
Figure 12:
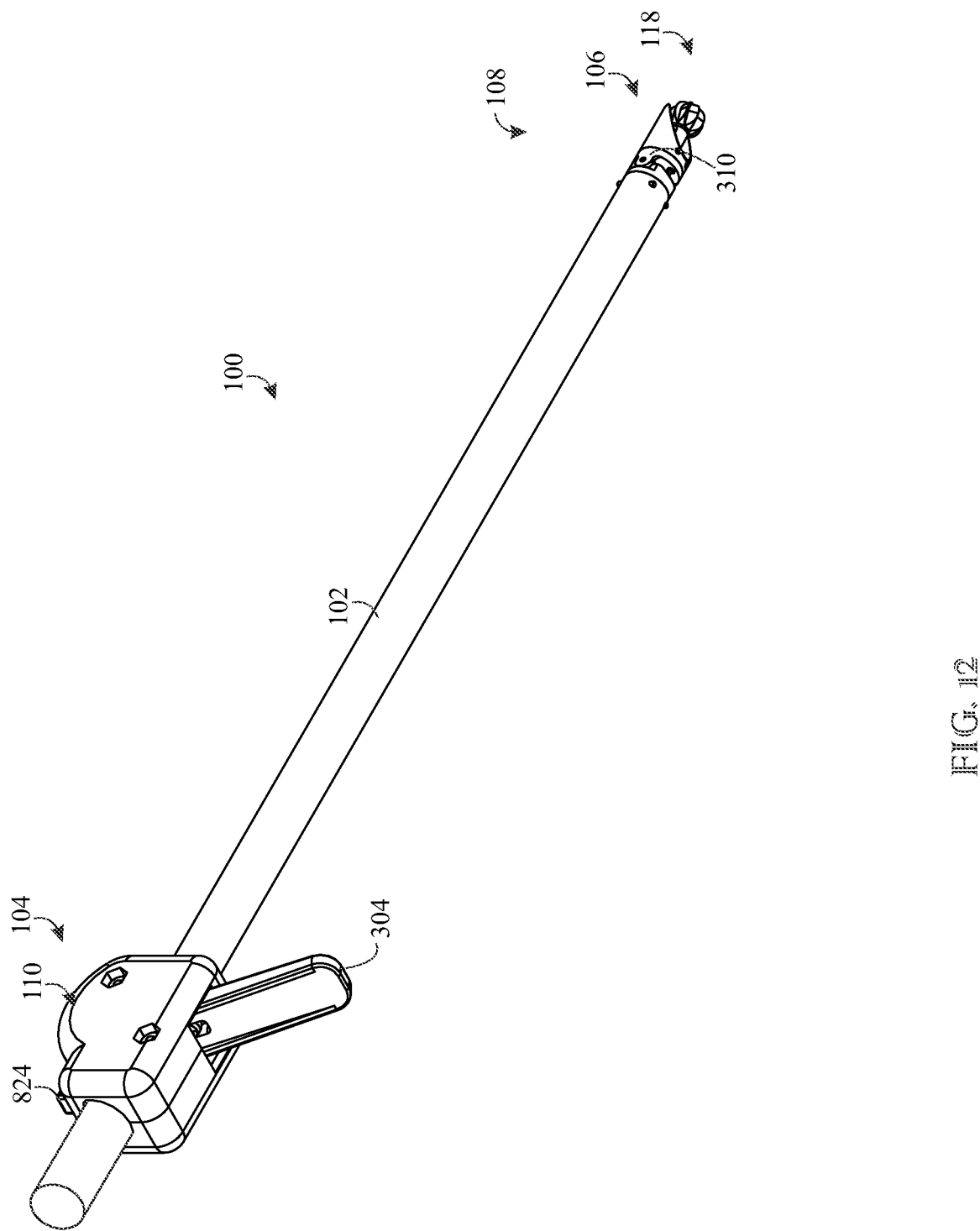
FIG. 12 presents a bottom perspective view of the articulating cutting tool of FIG. 11, in accordance with aspects of the present disclosure.
Figure 15:
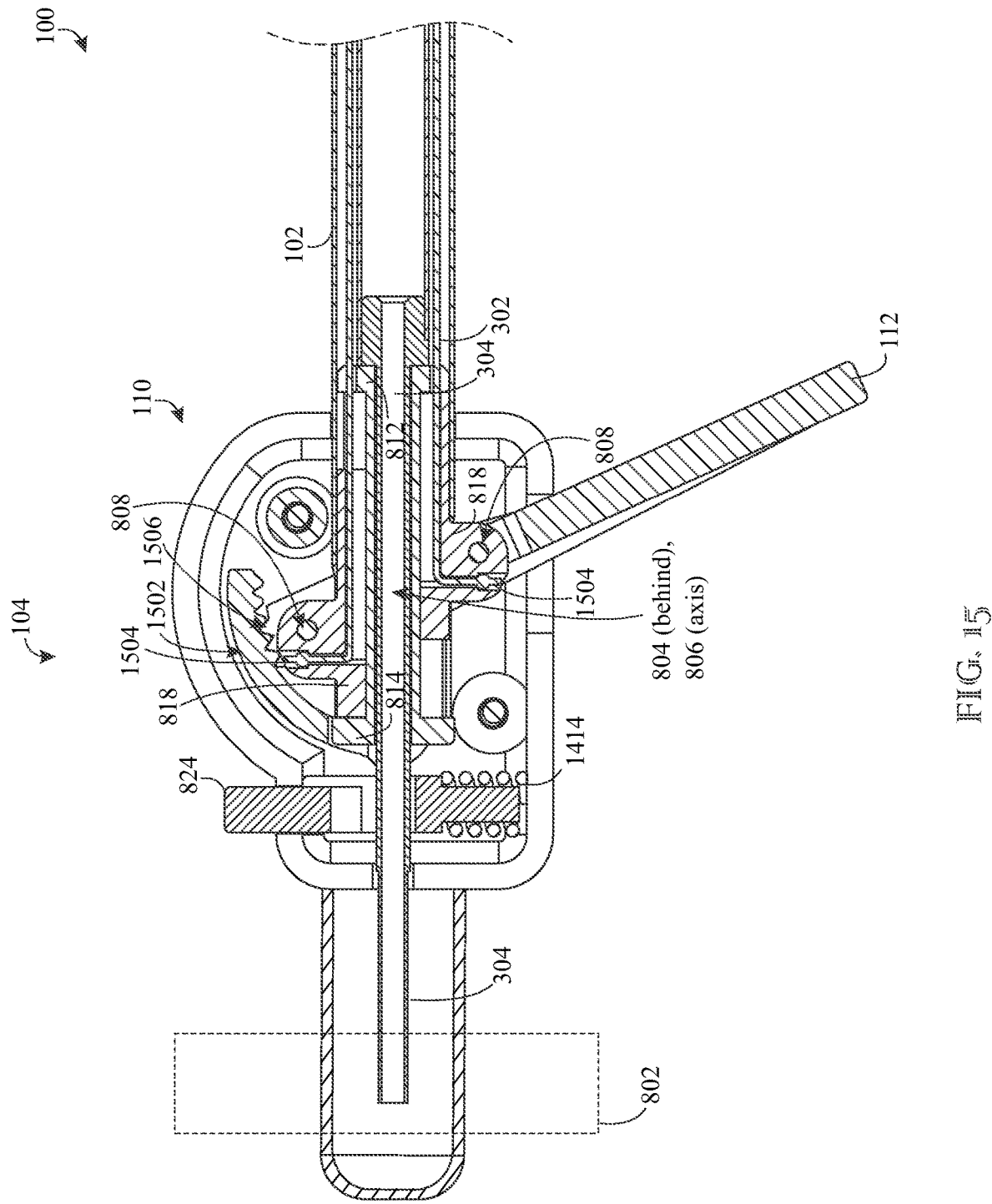
FIG. 15 presents a cross sectional view of a controller of the articulating cutting tool of FIG. 11, where the cross section is taken along longitudinal sectional plane 15-15 of FIG. 11, in accordance with aspects of the present disclosure.

Turning to the exemplary tool of FIG. 11, the articulating rotary cutting tool 100 may further include a second cable 316 attached to a second cable-trigger connection point 808 on the trigger 112, such that the second cable-trigger connection point 808 is opposite to the first cable-trigger connection point 808 of the first cable 302 with respect to the trigger pivotation axis 806 (FIG. 15). The second cable-trigger connection point 808 may be spaced away from the trigger pivotation axis 806, such that operating the trigger 112 causes the first cable-trigger connection point 808 and the second cable-trigger connection point 808 to displace in opposite directions to selectively articulate the cutting head 106 between non-articulated 118 and articulated 1002 positions.

The controller may include a toothed arm 1502, such that pushing a button 824 displaces the toothed arm 1502 (FIG. 15). A proximal end 1506 of the trigger 112 may be configured to snap into notches between teeth 816 of the toothed arm 1502 such that pulling or pushing the trigger 112 causes the proximal end 1506 of the trigger 112 to snap into a next notch, respectively. Operating the button 824 may release pressure between the proximal end 1506 of the trigger 112 and the toothed arm 1502 to allow the trigger 112 to more freely move with respect to the toothed arm 1502. The toothed arm 1502 may be curved, matching an arc travelable by the proximal end 1506 of the trigger 112.

The button 824 may be configured to receive the drive shaft 304 freely therethrough. The button 824 may include two sets of horizontal lateral extensions 1402 (FIG. 14), one set on each side, such that two opposing longitudinal extensions 1404 of the toothed arm 1502 are each respectively received in a gap 1406 between each set of horizontal extensions 1402 of the button 824. This allows the button 824 to press down and press up on the longitudinal extensions 1404 of the toothed arm 1502 via the horizontal extensions 1402 of the button 824.

The toothed arm 1502 may arc over the outer shaft 102 and/or the drive shaft 304 (FIG. 14), and be pivotably attached to a toothed arm attachment point 1408 at opposing outer surfaces of the outer shaft 102 between the longitudinal extensions 1404 and a distal portion of the toothed arm 1502, such that pressing down on the longitudinal extensions 1404 via the button 824 and upper horizontal extensions of the button 824 causes the distal portion to rise. The button 824 may be spring biased laterally upward (FIG. 15) via a spring 1414 to bias the longitudinal extensions upward via lower horizontal extensions of the button 824, for maintaining an appropriate pressure between the distal portion of the toothed arm 1502 and the proximal end of the trigger 112. Therefore, the toothed arm attachment point 1408 may be a fulcrum point for pivoting the toothed arm 1502 according to or in response to pressing or releasing the button 824.

The first and second cables each may have ball ends 1504 to prevent the cables from passing through or slipping out of their respective connection points at the controller and the articulable cutting head 106 (FIGS. 15 and 17).

Figure 14:
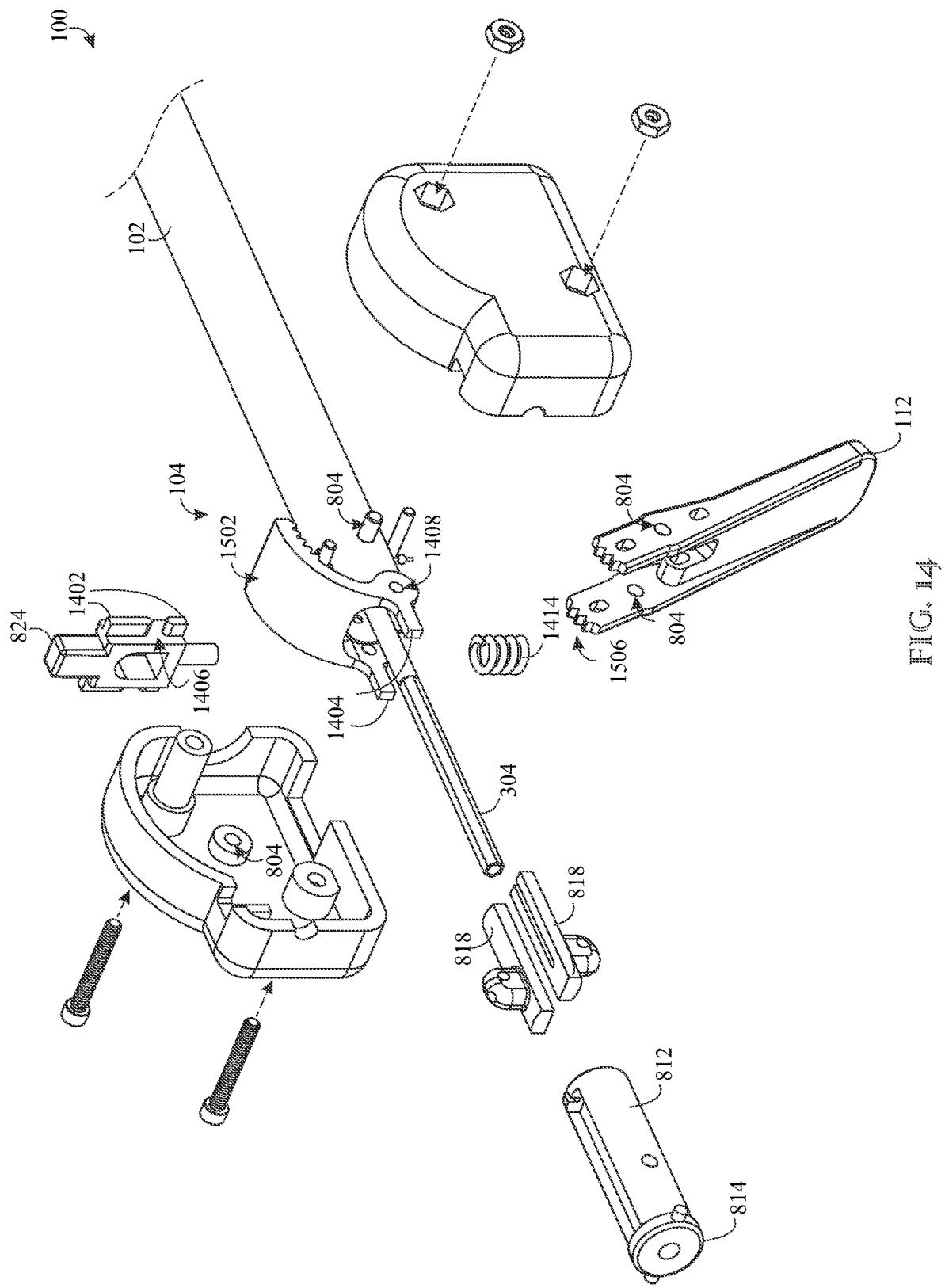
FIG. 14 presents an exploded view of various parts of proximal portions of the articulating cutting tool of FIG. 11, in accordance with aspects of the present disclosure.

It is to be understood that the configuration of the controller shown in FIGS. 14 and 15 may work synergistically with the flexible spring joint shown in FIG. 11, such that the articulated slide mechanism of the controller includes two surfaces 818 having constrained translation capability attached to the trigger 112 to efficiently articulate the head while also providing constraint to flexion and extension of the head in the articulated position due to the constrained translation of the two surfaces 818. This prevents the articulated head from excessively flexing or extending inadvertently during use (e.g. it will hold the articulation steady in a locked position).

A proximal end of the drive shaft 304 may be covered by a housing 114 (FIG. 1). The controller 110 may include a housing 116 to secure its components, while exposing the button 824, the trigger 112, a proximal portion of the drive shaft 304, the housing 114 of the drive shaft 304, forward or distal portions of the outer shaft 102, and the articulable cutting head 106. A guard or sheath 314 may be fixedly attached to the articulable support 310 to protect upper portions of the bit 308 from contacting unwanted surfaces, or to block debris (FIG. 3).

It is to be understood that, for clarity, the term pivoting or pivotation may refer to rotating or rotation having a lateral axis of rotation, and rotating or rotation may refer to rotating or rotation having a longitudinal axis of rotation, with respect to a longitudinal axis of the device or outer shaft. Further it is to be understood that descriptions of features, functions, elements, and structures, of FIGS. 1-10 may also apply to features, functions, elements, and structures of FIGS. 11-17, and vice-versa without departing from the spirit and scope of the present disclosure.

Further, it is to be understood that the term "articulating" may refer to causing the articulable cutting head to articulate. For example the trigger may hold an articulating position, to cause the articulable cutting head to hold an articulated position.

The disclosed articulating joint may be a constant velocity joint, providing a constant velocity of bit rotation in both an articulated and non-articulated position. The joint may be a hex ball joint (i.e. multi-faceted ball) as shown in FIGS. 3, 5-7, 9, and 10. The non-spring-biased trigger of FIGS. 11-17 may be referred to, and have the functions of, a mirror detented articulating slide. It is to be understood that where "hex ball" is mentioned herein, this may refer to a multi-faceted ball and the spirit and scope of the invention is not limited to hex ball joints.

It is to be understood that the rotary cutting bit 308 may be referred to as a burr, a burr bit, cutting bit, or a drill bit, without departing from the scope of this disclosure. The device may generally be referred to as an athroscopic articulating burr.

In conclusion, disclosed is an articulating rotary cutting tool. Unlike conventional arthroscopic bone burrs, this disclosed tool enters a joint but can be flexible to allow improved efficiency of bone removal. The invention can be used for hip, knee, ankle, or shoulder arthroscopy. Current problems with standard burr design include a fixed angle position, and the invention solves this problem by providing a constant velocity joint allowing a cutting bit to articulate while maintaining good strength and stability.

The disclosed device may be inserted with its head in a non-articulated position, and then once inserted into a target joint the device's head may be then articulated to remove desired area of bone. The articulating feature allows access through a smaller diameter portal compared to prior art devices since the device can be inserted in a collinear non-articulated position, and allows access to complex areas of anatomy for drilling bone, or performing tissue resection due to the articulating feature of the head or tip of the device. The device may be used for drilling, resection, RF, or other aspects of surgery such as an insertion of an implant.

The joint 502 may be a hex-ball joint, for hex ball articulation of the head of the device, providing an articulating rotary burr. Such a hex-ball joint provides a constant velocity of rotational motion along a cutting or drilling rotational axis of a rotary cutting bit. In one example, a spring coil (e.g. in a flexible spring joint) is used in an articulating rotary head to provide a constant velocity of rotational motion to a burr at both an articulated and non-articulated angle. A trigger assembly (i.e. controller) may include an articulated slide mechanism of two surfaces attached to a trigger to efficiently articulate the head while also providing a constraint to flexion and extension of the head in an articulated position. This can be seen in the trigger assembly of FIGS. 14 and 15, which will prevent a spring-joint version of the articulating head from excessively flexing or extending inadvertently during use (holding articulation steady in a locked position).

The articulating head may have a constrained hinge that allows motion only in one plane, as a non-limiting example.

The device also may have the ability to interchange any of the herein disclosed variations of assemblies for different iterations of the device. For example, a non-spring biased trigger (e.g. articulated slide mechanism) may be used with a non-spring joint of the head, and the spring joint of the head may be used with the spring biased trigger, and vice-versa, without departing from the scope of this disclosure.

It is to be understood that the disclosed device does not have the limitations found in U-Joints. For example, U-joints are limited in their ability to accomplish rotational motion in an articulated position, unlike the device of this disclosure.

The disclosed device allows the following advantages over the prior art, and more particularly universal joint burrs: higher stability at high speeds, less metallic wear debris produced, less vibration, the ability to reach much higher burring speeds safely, a hex ball constant velocity joint configuration or the flexible spring configuration having fewer intricate parts and being easier to manufacture than a configuration involving U-joint couplings, allowing lower cost of production, allowing the device to be a disposable instead of being a multiple use device which provides better profit for a manufacturing company, allowing lower cost in surgery, and having a more simplified articulating design which is more cost effective.

Both the above disclosed hex ball configuration (FIGS. 3, 5-7, 9, and 10) and flexible spring configuration (FIGS. 16 and 17) allow for articulation of the rotary head while running at a constant velocity at high speeds. The articulating head may have a constrained hinge that allows motion only in one plane. The trigger assembly may include articulating sliding surfaces (FIGS. 14 and 15) attached to cables which provide dual constraint to excessive flexion or extension of the articulating head to effectively prevent it from moving inadvertently in the locked position. The trigger assembly may be designed to have a single spring loaded button 824 (FIG. 8) that will straighten the articulating head with a simple push of the button 824, thereby easing control and use of the articulating rotary tool.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An articulating rotary cutting tool, comprising:
   an outer shaft having a proximal end and a distal end;
   at the distal end, a selectively articulable cutting head that is configured to articulate about a joint;
   at the proximal end, a controller;
   a longitudinal structure extending between the articulable cutting head and the controller through the outer shaft;
   a drive shaft within the outer shaft extending between the proximal end and the distal end, the drive shaft attached to or having an integrated rotary socket at the distal end for driving the rotary socket, the longitudinal structure located between the drive shaft and the outer shaft, the drive shaft connectable to a driver at a proximal end of the drive shaft for being driven to translate rotational motion delivered by the driver to the articulable cutting head; and
   a distal connector configured to connect the articulable cutting head to the distal end of the outer shaft, the distal connector including a space to receive the longitudinal structure therethrough for attaching a distal end of the longitudinal structure to the articulable cutting head;
   wherein the longitudinal structure is attached to the controller and the articulable cutting head such that operating the controller causes the longitudinal structure to displace to selectively articulate the articulable cutting head about the joint; and
   wherein the articulable cutting head includes a rotary cutting bit and an articulable support that the rotary cutting bit rotates in relation to, the rotary cutting bit being configured to be rotationally driven by the rotary socket such that the rotary cutting bit is rotationally drivable by the rotary socket in both a non-articulated and an articulated position.

2. The articulating rotary cutting tool of claim 1, wherein the rotary cutting bit and the articulable support articulate together upon the controller being operated.

3. The articulating rotary cutting tool of claim 1, wherein the rotary socket is located inside the outer shaft at the distal end of the outer shaft.

4. The articulating rotary cutting tool of claim 1, wherein the drive shaft and the rotary socket rotate about a longitudinal axis of rotation in relation to the outer shaft and the longitudinal structure.

5. The articulating rotary cutting tool of claim 1, wherein the drive shaft and rotary socket rotate in relation to the outer shaft and the longitudinal structure to cause the rotary cutting bit to rotate in relation to the articulable support of the articulable cutting head in both an articulated and non-articulated position of the articulable cutting head.

6. The articulating rotary cutting tool of claim 1, wherein the longitudinal structure translates longitudinally in relation to the outer shaft to cause the articulable cutting head to articulate.

7. The articulating rotary cutting tool of claim 1, wherein the joint has a joint axis of pivotation that passes through the rotary socket.

8. The articulating rotary cutting tool of claim 1, wherein the rotary cutting bit pivotably attaches at a pivotal bit attachment point to a distal end of the rotary socket, such that the rotary cutting bit articulates by pivoting about the pivotal bit attachment point, about a bit axis of pivotation.

9. The articulating rotary cutting tool of claim 1, wherein the articulable support is pivotably attached to the distal connector at opposing pivotal support attachment points, allowing the articulable support to pivotally articulate by pivoting about a support axis of pivotation that passes through a pivotal bit attachment point of the rotary cutting bit.

10. The articulating rotary cutting tool of claim 1, wherein the articulable support and the rotary cutting bit share an axis of pivotation through a pivotal attachment point of the articulable support at the distal connector, and through a pivotal attachment point of the rotary cutting bit at the rotary socket.

11. The articulating rotary cutting tool of claim 10, wherein the axis of pivotation passes through both pivotal attachment points of the articulable support and the rotary cutting bit.

12. The articulating rotary cutting tool of claim 1, wherein the rotary cutting bit includes a rotary cutting bit groove, and the articulable support is configured to receive two parallel opposing bit pins on opposing sides of the articulable support, such that the rotary cutting bit is supported by the two bit pins contacting the rotary cutting bit groove while the rotary cutting bit is driven.

13. The articulating rotary cutting tool of claim 1, wherein the rotary socket includes a groove, and the outer shaft is configured to receive two parallel opposing socket pins on opposing sides of the outer shaft, such that the rotary socket is supported by the socket pins contacting the rotary socket groove while the rotary socket is driven.

14. The articulating rotary cutting tool of claim 1, wherein the rotary cutting bit is flexibly attached to the rotary socket by an intermediate flexible structure, the flexible structure acting as a flexible spring joint.

15. The articulating rotary cutting tool of claim 14, wherein the flexible structure is a spring.

16. The articulating rotary cutting tool of claim 1, wherein the controller includes a trigger that is pivotably attached to the outer shaft at opposing pivotal trigger attachment points such that the trigger pivots about a trigger pivotation axis.

17. The articulating rotary cutting tool of claim 16, wherein a proximal end of the longitudinal structure is attached to the trigger at a longitudinal structure-trigger connection point, where the longitudinal structure-trigger connection point is a point that is spaced away from the trigger pivotation axis, such that pulling the trigger causes the longitudinal structure-trigger connection point to displace in relation to the trigger pivotation axis.

18. The articulating rotary cutting tool of claim 16, wherein the controller includes a toothed slide connected to the trigger, and a proximal end plug that fixedly fits in the proximal end of the outer shaft, such that pulling the trigger displaces the toothed slide, wherein the proximal end plug has an external plug portion configured to snap into notches between teeth of the toothed slide such that pulling the trigger causes the external plug portion of the proximal end plug to snap into a next notch of the notches.

19. The articulating rotary cutting tool of claim 18, wherein the proximal end plug is configured to receive the drive shaft freely therethrough.

20. The articulating rotary cutting tool of claim 18, wherein a longitudinal structure-trigger connecting slide is included in the controller to connect the longitudinal structure to the trigger at the longitudinal structure-trigger connection point, where the trigger is pivotably attached to the longitudinal structure-trigger connecting slide, where the longitudinal structure-trigger connecting slide is configured to receive the longitudinal structure through a receiving space of the longitudinal structure-trigger connecting slide, where the longitudinal structure-trigger connecting slide also is connected to the toothed slide for displacing the toothed slide, and where pulling the trigger translates the longitudinal structure-trigger connecting slide longitudinally in a direction away from the distal end of the outer shaft, to cause the toothed slide to translate.

21. The articulating rotary cutting tool of claim 18, wherein the longitudinal structure-trigger connecting slide is pivotably connected to the toothed slide to reduce lateral forces applied to the toothed slide by the longitudinal structure-trigger connecting slide translating.

22. The articulating rotary cutting tool of claim 9, wherein the articulating rotary cutting tool further comprises:
a second longitudinal structure that is attached at one end to a spring at the proximal end of the outer shaft and attached at an opposite end of the second longitudinal structure to an upper portion of the articulable cutting head laterally above the pivotal support attachment points and laterally above a pivotal bit attachment point, the second longitudinal structure passing through the distal connector, the spring biasing the articulable cutting head toward a non-articulated position by applying a longitudinal biasing force having a force vector pointed away from the articulable cutting head, causing a trigger to be spring biased toward a non-articulating position, since a forward biasing force on the trigger is mechanically dependent on the spring biasing force applied by the spring through the second longitudinal structure, through the articulable cutting head, and through the first longitudinal structure.

23. The articulating rotary cutting tool of claim 22, wherein the two longitudinal structures are vertically aligned and parallel.

24. The articulating rotary cutting tool of claim 22, wherein the spring bias applied by the second longitudinal structure to the trigger by way of pulling the articulable cutting head causes teeth of a toothed slide to be longitudinally force-biased against an external plug portion, such that pulling the trigger can overcome the spring bias and snap the external plug portion between the teeth, and such that the trigger is selectively lockable into a next notch between the teeth.

25. The articulating rotary cutting tool of claim 1, wherein the controller further includes a spring biased button that arcs over the drive shaft and contacts a toothed slide such that when the button is pressed the toothed slide translates laterally away from the drive shaft such that the toothed slide releases from being longitudinally forced against an external plug portion causing a trigger to translate back to the non-articulating position due to the spring bias applied by the spring and the second longitudinal structure, allowing a user to subsequently pull the trigger to selectively lock the toothed slide behind the external plug portion in increments set by a spacing of the teeth to one or more articulated positions set by the spacing of the teeth, and such that the user may press the spring biased button again to release the toothed slide from being longitudinally forced against the external plug portion and be displaced back into the non-articulating position by way of a spring force applied through the second longitudinal structure by the spring.

26. The articulating rotary cutting tool of claim 1, wherein the controller further includes:
a second spring biasing a toothed slide upwards, laterally, to allow teeth to be laterally forced against an external plug portion and to allow the external plug portion to contact a top surface of the toothed slide, to allow the teeth to apply a longitudinal force against the external plug portion due to a spring bias of a first spring, such that the button contacts a top surface of the toothed slide to cause the toothed slide to displace downward against the second spring when the button is pressed to release the teeth from being longitudinally forced against the external plug portion.

27. The articulating rotary cutting tool of claim 26, wherein the second spring receives a perpendicular, laterally, and downwardly extending portion of the toothed slide such that the second spring applies a longitudinal resistive force to the downwardly extending portion of the toothed slide when the trigger is pulled.

28. The articulating rotary cutting tool of claim 26, wherein the proximal end plug houses the first spring and a front portion of the longitudinal structure-trigger connecting slide, and a proximal end of the first spring is attached to a proximal portion of the proximal end plug.

29. The articulating rotary cutting tool of claim 1, wherein the articulating rotary cutting tool further comprises:
a second longitudinal structure attached to a second longitudinal structure-trigger connection point on a trigger, such that the second longitudinal structure-trigger connection point is opposite to a first longitudinal structure-trigger connection point of a first longitudinal structure with respect to a trigger pivotation axis, where the second longitudinal structure-trigger connection point is spaced away from the trigger pivotation axis, such that operating the trigger causes the first longitudinal structure-trigger connection point and the second longitudinal structure-trigger connection point to displace in opposite directions to selectively articulate the cutting head between non-articulated and articulated positions.

30. The articulating rotary cutting tool of claim 1, wherein the controller includes a toothed arm, such that pushing a button displaces the toothed arm, wherein a proximal end of the trigger is configured to snap into notches between teeth of the toothed arm such that pulling or pushing the trigger causes the proximal end of the trigger to snap into a next notch, respectively, wherein operating the button releases pressure between the proximal end of the trigger and the toothed arm to allow the trigger to more freely move with respect to the toothed arm.

31. The articulating rotary cutting tool of claim 30, wherein the toothed arm is curved, matching an arc travelable by the proximal end of a trigger.

32. The articulating rotary cutting tool of claim 1, wherein a button is configured to receive the drive shaft freely therethrough, and includes two sets of horizontal lateral extensions, one set on each side, such that two opposing longitudinal extensions of a toothed arm are each respectively received in a gap between each set of horizontal extensions of the button, to allow the button to press down and up on longitudinal extensions of the toothed arm.

33. The articulating rotary cutting tool of claim 1, wherein a toothed arm arcs over, and is pivotably attached to a toothed arm attachment point at opposing outer surfaces of the outer shaft between longitudinal extensions and a distal portion of the toothed arm, such that pressing down on the longitudinal extensions via a button and upper horizontal extensions of the button causes the distal portion to rise, and wherein the button is spring biased laterally upward via a spring to bias the longitudinal extensions upward via lower horizontal extensions of the button, for maintaining an appropriate pressure between the distal portion of the toothed arm and the proximal end of the trigger, the toothed arm attachment point being a fulcrum point for the toothed arm pivoting according to pressing or releasing the button.

34. The articulating rotary cutting tool of claim 1, wherein the longitudinal structures each have ball ends to prevent the longitudinal structures from passing through their respective connection points.

35. The articulating rotary cutting tool of claim 1, wherein a proximal end of the drive shaft is covered by a housing.

36. The articulating rotary cutting tool of claim 25, wherein the controller includes a housing to secure its components, while exposing the button, the trigger, a proximal portion of the drive shaft, the housing of the drive shaft, forward portions of the outer shaft, and the articulable cutting head.

37. The articulating rotary cutting tool of claim 1, wherein a sheath may be fixedly attached to the articulable support to block non-cutting portions of the articulable support.

38. An articulating rotary cutting tool, comprising:
an outer shaft having a proximal end and a distal end;
at the distal end, a selectively articulable cutting head that is configured to articulate about a joint;
at the proximal end, a controller;
a longitudinal structure extending between the articulable cutting head and the controller through the outer shaft;
a drive shaft within the outer shaft extending between the proximal end and the distal end, the drive shaft attached to or having an integrated rotary socket at the distal end for driving the rotary socket, the longitudinal structure located between the drive shaft and the outer shaft, the drive shaft connectable to a driver at a proximal end of the drive shaft for being driven to translate rotational motion delivered by the driver to the articulable cutting head; and
a distal connector configured to connect the articulable cutting head to the distal end of the outer shaft, the distal connector including a space to receive the longitudinal structure therethrough for attaching a distal end of the longitudinal structure to the articulable cutting head,
wherein the longitudinal structure is attached to the controller and the articulable cutting head such that operating the controller causes the longitudinal structure to displace to selectively articulate the articulable cutting head about the joint;
wherein the articulable cutting head includes a rotary cutting bit and an articulable support that the rotary cutting bit rotates in relation to, the rotary cutting bit being configured to be rotationally driven by the rotary socket such that the rotary cutting bit is rotationally drivable by the rotary socket in both a non-articulated and an articulated position;
wherein the rotary cutting bit and the articulable support articulate together upon the controller being operated; and
wherein the rotary cutting bit pivotably attaches at a pivotal bit attachment point to a distal end of the rotary socket, such that the rotary cutting bit articulates by pivoting about the pivotal bit attachment point, about a bit axis of pivotation.

39. A method of using an articulating rotary cutting tool, the method comprising:
providing an articulating rotary cutting tool, the tool comprising:
an outer shaft having a proximal end and a distal end;
at the distal end, a selectively articulable cutting head that is configured to articulate about a joint;
at the proximal end, a controller;
a longitudinal structure extending between the articulable cutting head and the controller through the outer shaft;
a drive shaft within the outer shaft extending between the proximal end and the distal end, the drive shaft attached to or having an integrated rotary socket at the distal end for driving the rotary socket, the longitudinal structure located between the drive shaft and the outer shaft, the drive shaft connectable to a driver at a proximal end of the drive shaft for being driven to translate rotational motion delivered by the driver to the articulable cutting head;
wherein the longitudinal structure is attached to the controller and the articulable cutting head such that operating the controller causes the longitudinal structure to displace to selectively articulate the articulable cutting head about the joint; and
wherein the articulable cutting head includes a rotary cutting bit and an articulable support that the rotary cutting bit rotates in relation to, the rotary cutting bit being configured to be rotationally driven by the rotary socket such that the rotary cutting bit is rotationally drivable by the rotary socket in both a non-articulated and an articulated position; and wherein the rotary socket is located inside the outer shaft at the distal end of the outer shaft;

wherein the controller includes a trigger that causes articulation in one direction and a button that causes articulation in an opposite direction;

pulling the trigger to cause the cutting head to articulate in a first direction and lock into place selectively; and pushing a button to cause the cutting head to articulate in a second direction opposite the first direction after the cutting head is locked in place.

\* \* \* \* \*